United States Patent
Igarashi et al.

(10) Patent No.: US 10,869,124 B2
(45) Date of Patent: Dec. 15, 2020

(54) INFORMATION PROCESSING APPARATUS, CONTROL METHOD, AND RECORDING MEDIUM

(71) Applicant: SONY CORPORATION, Tokyo (JP)

(72) Inventors: Go Igarashi, Tokyo (JP); Kazuma Yoshii, Tokyo (JP); Junya Suzuki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/606,367

(22) PCT Filed: Mar. 23, 2018

(86) PCT No.: PCT/JP2018/011745
§ 371 (c)(1),
(2) Date: Oct. 18, 2019

(87) PCT Pub. No.: WO2018/216339
PCT Pub. Date: Nov. 29, 2018

(65) Prior Publication Data
US 2020/0077183 A1 Mar. 5, 2020

(30) Foreign Application Priority Data
May 23, 2017 (JP) .................................. 2017-101968

(51) Int. Cl.
*H04R 1/46* (2006.01)
*A61B 5/00* (2006.01)
(Continued)

(52) U.S. Cl.
CPC ............. *H04R 1/46* (2013.01); *A61B 5/0002* (2013.01); *A61B 5/0531* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 6,356,639 B1* | 3/2002 | Ishito | ...................... | G10L 21/04 381/17 |
| 2009/0296965 A1* | 12/2009 | Kojima | ................ | H04R 25/407 381/312 |

(Continued)

FOREIGN PATENT DOCUMENTS

| | | |
|---|---|---|
| CN | 106037702 A | 10/2016 |
| EP | 2944263 A1 | 11/2015 |

(Continued)

OTHER PUBLICATIONS

Vital Sensor Module and opeartion methid therefor, Satomi Takeshi, English translation JP2016214731A, May 25, 2015, 19 pages (Year: 2015).*

(Continued)

*Primary Examiner* — Duc Nguyen
*Assistant Examiner* — Assad Mohammed
(74) *Attorney, Agent, or Firm* — Chip Law Group

(57) ABSTRACT

Provided is an information processing apparatus that is used by being adhered to the body of a user. The information processing apparatus includes a sound pickup sensor that has a sound pickup function, a communicating part that wirelessly transmits audio data picked up by the sound pickup sensor to the outside, a control part that controls the sound pickup sensor and the communicating part, a power source part that supplies a power source to at least one of the sound pickup sensor, the communicating part, or the control part, a housing part that accommodates therein at least one of the sound pickup sensor, the communicating part, the control part, or the power source part, and an adhering part that fixes (Continued)

the housing part to the user. The sound pickup part picks up a sound of the user using, for example, flesh conduction or bone conduction.

18 Claims, 16 Drawing Sheets

(51) Int. Cl.
  *A61B 7/04* (2006.01)
  *G06F 3/16* (2006.01)
  *H04R 1/02* (2006.01)
  *H04R 1/04* (2006.01)
  *H04R 3/00* (2006.01)

(52) U.S. Cl.
  CPC .......... *A61B 5/4266* (2013.01); *A61B 5/6815* (2013.01); *A61B 5/6833* (2013.01); *A61B 5/6844* (2013.01); *A61B 5/742* (2013.01); *A61B 7/04* (2013.01); *G06F 3/16* (2013.01); *H04R 1/025* (2013.01); *H04R 1/04* (2013.01); *H04R 3/00* (2013.01); *A61B 2560/0214* (2013.01); *A61B 2562/0204* (2013.01)

(56) References Cited

U.S. PATENT DOCUMENTS

| | | | | |
|---|---|---|---|---|
| 2014/0303521 | A1* | 10/2014 | Nakamura | A61B 7/003 600/586 |
| 2015/0173672 | A1* | 6/2015 | Goldstein | A61B 5/0205 600/301 |
| 2015/0327810 | A1* | 11/2015 | Horii | A61B 7/02 600/586 |
| 2016/0302680 | A1* | 10/2016 | Narusawa | A61B 5/742 |
| 2016/0367190 | A1* | 12/2016 | Vaitaitis | A61B 7/04 |

FOREIGN PATENT DOCUMENTS

| | | | | |
|---|---|---|---|---|
| EP | 3081157 | A1 | | 10/2016 |
| JP | 2004-523289 | A | | 8/2004 |
| JP | 2006-345269 | A | | 12/2006 |
| JP | 2007-117268 | A | | 5/2007 |
| JP | 2007117268 | A | * | 5/2007 |
| JP | 2013-103040 | A | | 5/2013 |
| JP | 2015-217045 | A | | 12/2015 |
| JP | 2016-202347 | A | | 12/2016 |
| JP | 2016-214731 | A | | 12/2016 |
| JP | 2016214731 | A | * | 12/2016 |
| WO | 2013/073311 | A1 | | 5/2013 |
| WO | 2016/063587 | A1 | | 4/2016 |

OTHER PUBLICATIONS

Biological information device, Kuroda Masaaki, English translation of JP2007-117268A, May 17, 2007, 48 pages (Year: 2007).*
International Search Report and Written Opinion of PCT Application No. PCT/JP2018/011745, dated May 29, 2018, 10 pages of ISRWO.

* cited by examiner

FIG.7

| | ADHESION DETECTING PART | SOUND PICKUP SENSOR | SPEAKER | IMAGE SENSOR | DISPLAYING PART | BRAIN WAVE SENSOR | ELECTRIC OUTPUT PART |
|---|---|---|---|---|---|---|---|
| TEMPLE | ○ | ○ | ○ | | | ○ | △ |
| GLABELLA | ○ | | | ○ | | | |
| BACK OF EAR | ○ | ○ | ○ | | | ○ | △ |
| NECK | ○ | ○ | | | | | |
| ROOT OF NECK | ○ | ○ | ○ | | | | |
| UPPER ARM/ FOREARM | ○ | | △ | | ○ | | |
| WRIST | ○ | | △ | | ○ | | |
| ABDOMEN | ○ | | | | | | ○ |

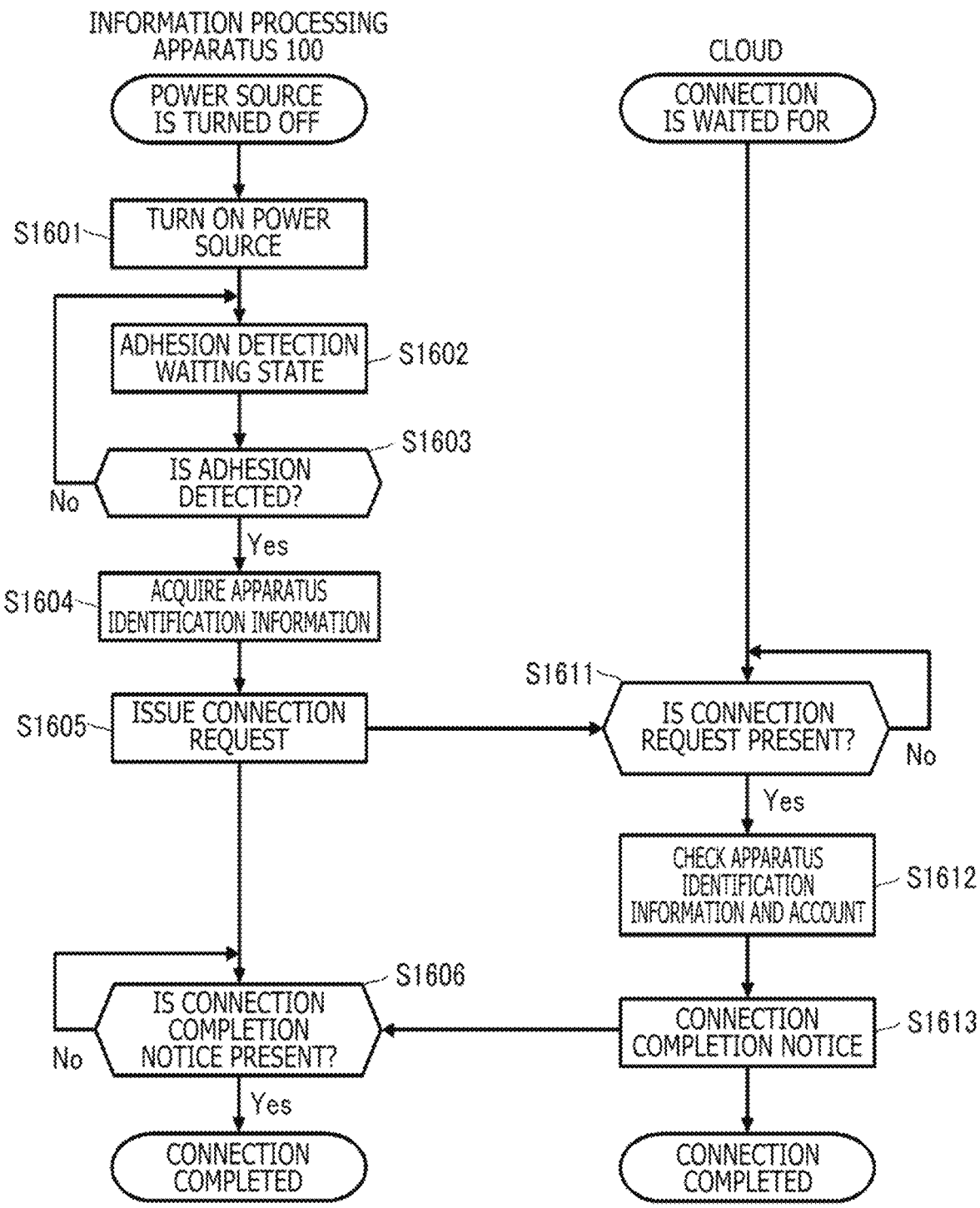

INFORMATION PROCESSING APPARATUS, CONTROL METHOD, AND RECORDING MEDIUM

CROSS REFERENCE TO RELATED APPLICATIONS

This application is a U.S. National Phase of International Patent Application No. PCT/JP2018/011745 filed on Mar. 23, 2018, which claims priority benefit of Japanese Patent Application No. JP 2017-101968 filed in the Japan Patent Office on May 23, 2017. Each of the above-referenced applications is hereby incorporated herein by reference in its entirety.

TECHNICAL FIELD

The technique disclosed herein relates to an information processing apparatus that is used by being attached to the body of a user, a control method therefor, and a recording medium.

BACKGROUND ART

A wearable device have recently been prevailing that is used by being attached to various points of the body of a user such as an arm and the head. The wearable device is used for detection of biological information, position information, and other users' states, recoding such as imaging or recording of the sound of the user's surrounding, presentation of various types of information to the user using a sound etc., and the like. The wearable device is used in a wide range of fields such as, for example, a field of lifelogging and a field of supporting sports.

A neckband-type wearable device has been proposed that is attached to be worn around the neck of a user using, for example, an attachment unit that runs half around the neck of the user from both of the left and right sides of the neck to the back side thereof (on the side of the user's back) (for example, see PTL 1).

The wearable device includes an operation part that enables a touch operation and a sliding operation with which the user performs an input operation, and has a sound recognition function, and the like. The user can give various instructions to the wearable device through the input operation or the sound input through the operation part, such as start or stoppage of capturing or recording of images, start or stoppage of sound reproduction, and requesting for information presentation or stoppage of the presentation.

CITATION LIST

Patent Literature

[PTL 1]
  WO 2016/063587
[PTL 2]
  JP-T-2004-523289
[PTL 3]
  JP-A-2006-345269

SUMMARY

Technical Problems

An object of the technique disclosed herein is to provide an information processing apparatus that is used by being attached to the body of a user, a control method therefor, and a recording medium.

Solution to Problems

A first aspect of the technique disclosed herein is an information processing apparatus including:
  a sound pickup sensor that has a sound pickup function;
  a communicating part that wirelessly transmits audio data picked up by the sound pickup sensor to the outside;
  a control part that controls the sound pickup sensor and the communicating part;
  a power source part that supplies a power source to at least one of the sound pickup sensor, the communicating part, or the control part;
  a housing part that accommodates therein at least one of the sound pickup sensor, the communicating part, the control part, or the power source part; and
  an adhering part that fixes the housing part to a user.

The sound pickup sensor is able to pick up the sound using flesh conduction of the user. Moreover, the information processing apparatus may further include an biological sensor that detects the biological information of the user, in which the control part may control processing for the audio data picked up by the sound pickup sensor on the basis of the biological information detected by the biological sensor.

Moreover, a second aspect of the technique disclosed herein is a control method for an information processing apparatus including a sound pickup sensor that has a sound pickup function; a communicating part that wirelessly transmits audio data picked up by the sound pickup sensor to the outside; a power source part that supplies a power source to at least one of the sound pickup sensor, the communicating part, or the control part; a housing part that accommodates therein at least one of the sound pickup sensor, the communicating part, the control part, or the power source part; and an adhering part that fixes the housing part to a user, and the control method includes steps of:
  processing the audio data picked up by the sound pickup sensor, and
  controlling transmission and reception processes through the communicating part.

Moreover, a third aspect of the technique disclosed herein is a recording medium that records thereon a computer program to control an information processing apparatus including a sound pickup sensor that has a sound pickup function; a communicating part that wirelessly transmits audio data picked up by the sound pickup sensor to the outside; a power source part that supplies a power source to at least one of the sound pickup sensor, the communicating part, or the control part; a housing part that accommodates therein at least one of the sound pickup sensor, the communicating part, the control part, or the power source part; and an adhering part that fixes the housing part to a user, in which the computer program is described in a computer readable format to cause a computer to execute steps of:
  processing the audio data picked up by the sound pickup sensor, and
  controlling transmission and reception processes through the communicating part.

Advantageous Effects of Invention

According to the technique disclosed herein, the information processing apparatus that is used by being attached to the body of a user, a control method therefor, and a recording medium can be provided.

In addition, the effect described herein is absolutely exemplification, and effects of the present invention are not limited to the above effect. Moreover, the present invention may further achieve any additional effects in addition to the above effect.

Other objects, features, and advantages of the technique disclosed herein will become more apparent from the following embodiment and details described later with reference to the accompanying drawings.

BRIEF DESCRIPTION OF DRAWINGS

FIG. 7 is a table indicating suitableness or unsuitableness of each of sensor elements and actuator elements in accordance with the adhesion point.

FIG. 16 is a diagram exemplifying a process procedure for connecting the information processing apparatus 100 and the cloud.

DESCRIPTION OF EMBODIMENT

Figure 1:
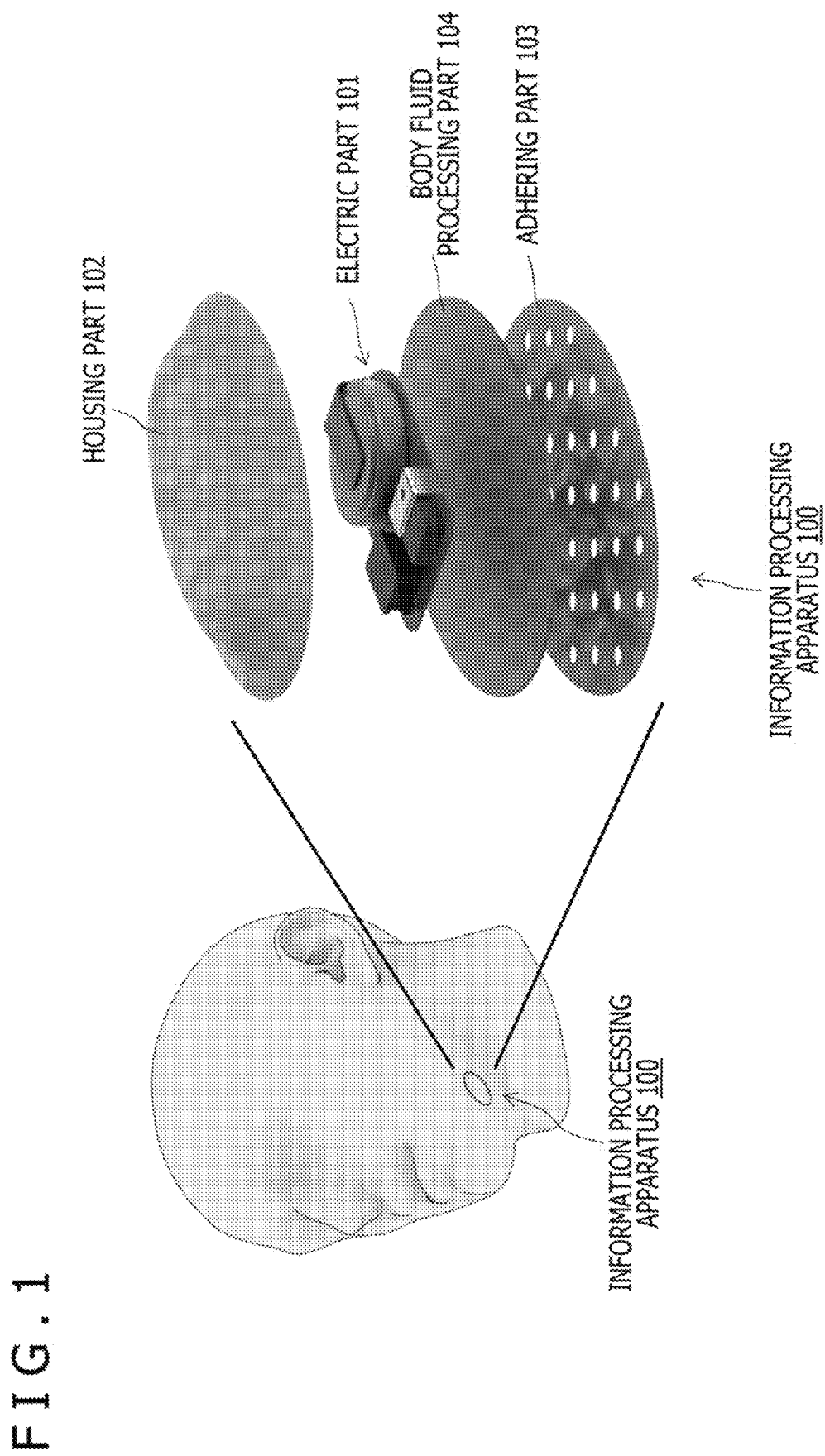
FIG. 1 is a diagram depicting the state where an information processing apparatus 100 adheres to a region beneath the jaw of a user and an exploded view of the information processing apparatus 100.

An embodiment of the technique disclosed herein will be described in detail below with reference to the drawings.

Wearable devices each used by being attached to an arm or the head are widely known such as a wristwatch-type information terminal and a spectacles-type information terminal. For example, the wristwatch-type information terminal is used by being wound in the vicinity of a wrist of a user like a wristwatch and provides many functions such as communication using characters such as an email, activity amount measurement and display of the measurement result such as a pedometer, and reproduction of music, in addition to the basic functions of a wristwatch. Moreover, the spectacles-type information terminal presents information in a portion of the field of view of the user having the spectacles-type information terminal attached thereto and the user can thereby always receive the information such as navigation and the latest news.

It is outwardly apparent for many of the conventional wearable devices each to be attached to a user. For example, the spectacles-type information terminal is significantly different in the shape from an ordinary spectacles for visual correction. The spectacles-type information terminal may therefore provide feeling of strangeness to the people around and it is worried that this obstacles prevalence of any wearable device. A method can also be considered according to which the wearable device is caused to be accepted by the user him/herself and the people around without any feeling of strangeness by using a worked-out design for the apparatus main body of the wearable device. Moreover, it is not easy to exclude from the user any psychological feeling of strangeness against the use of any apparatus in a new form.

An information processing apparatus to be used by being directly adhere to the surface (or the skin) of the body of a user will therefore be proposed herein below. The information processing apparatus caused to adhere to the surface of the body of the user has the minimum outward change, therefore does not need to provide any feeling of strangeness to the people around, and does not provide any feeling of attachment to the user him/herself as far as possible.

The information processing apparatus is basically configured as a physically single apparatus and is used by being adhered to any one region on the body of the user described above. As a modification example, the information processing apparatus is configured as an aggregation of two or more divided apparatuses each physically separated from each other, and the divided apparatuses are caused to adhere to two or more regions described above. In the latter case, the divided apparatuses are mutually connected to each other using wireless communication, biological communication, or the like, and are configured such that the divided apparatuses operate in cooperation with each other to function as one information processing apparatus. Hereinafter, however, description will be made being limited to that of the case where the information processing apparatus is configured as a physically single apparatus.

The information processing apparatus includes, as its basic components, a sound pickup sensor that has a sound pickup function, a communicating part that wirelessly transmits audio data picked up by the sound pickup sensor to the outside, a control part that controls the sound pickup sensor and the communicating part, a power source part that supplies a power source to an electric part including at least the sound pickup sensor, the communicating part, and the control part, a housing part that accommodates therein the electric part and the power source part, and an adhering part that fixes the housing part by causing the housing part to the surface of the body of a user.

An IoT (Internet of Things) device has no conventional input apparatus present therein such as a mouse and a keyboard, and a user interface (UI) using sound information is more dominant than that using character information. It can therefore be stated that the sound pickup sensor is one of the components essential to the information processing apparatus. The sound pickup sensor includes, for example, a small microphone.

In the case where a main body of the information processing apparatus is used by being adhered to a temple, the back of an ear, a region beneath the jaw, the neck, the root of the neck, or the vicinity of the vocal cords of the user such as the throat portion, the real voice of the user can effectively be collected including those through air conduction from the mouth, and flesh conduction or the bone conduction in the head. The information processing apparatus therefore easily provides a sound sensing function for lifelogging. Moreover, when the region beneath the jaw or the like is set to be the adhesion point, the information processing apparatus is inconspicuous and no feeling of strangeness has to be given to the people around.

FIG. 1 depicts, as an example, the state where the information processing apparatus 100 adheres to the region beneath the jaw of a user and an exploded view of the information processing apparatus 100. The exploded view of the information processing apparatus 100 however depicts, for convenience, the information processing apparatus 100 upside-down against that of the state where the information processing apparatus 100 adheres to the region beneath the jaw of the user.

A main body of the information processing apparatus 100 is hidden beneath the jaw of the user, substantially no outward change is therefore present, and no feeling of strangeness has to be provided to the people around.

The depicted information processing apparatus 100 includes: an electric part 101 that includes a substrate having circuit components mounted thereon such as a sound pickup sensor, a communicating part, a control part, and a power source part; a housing part 102 that accommodates the electric part 101; and an adhering part 103 that fixes the housing part 102 to the body of the user by causing the housing part 102 to adhere to the surface of the body of the user. Moreover, the depicted information processing apparatus 100 has a body fluid processing part 104 stacked therein on the adhering part 103.

It is preferred that the housing part 102 have flexibility taking into consideration that, when the housing part 102 is brought into contact with the body regions of the user other than the region to which the main body of the information processing apparatus 100 adheres and the body of each of the people around, the housing part 102 does not damage these bodies. The housing part 102 is constituted using a metallic or a non-metallic material while the housing part 102 needs to have radio wave permeability because the housing part 102 includes the communicating part.

Moreover, it is preferred that the surface (or the outer appearance face) of the housing part 102 be color-matched with the color of the skin such that the outward change in the region to which the main body of the information processing apparatus 100 adheres becomes minimal. Otherwise, the surface of the housing part 102 may be colored into a transparent color or painted into a fashionable color. Moreover, a pattern like that of a tattoo seal may be formed on the surface of the housing part 102 to express the personality of the user.

It is however assumed that the main body of the information processing apparatus 100 is used by being adhered to not only the region beneath the jaw of the user but also each of various points on the surface of the body of the user. The outer appearance shape of the housing part 102 or the main body of the information processing apparatus 100 may therefore be changed for each of the adhesion points, or a common outer appearance shape may be employed for all the adhesion points.

Moreover, it is preferred that the housing part 102 have a water-shedding property by using a water-shedding material, applying a water-shedding processing to the surface thereof, or the like. When the surface of the housing part 102 has no water-shedding property, body fluid secreted or discharged from the skin of the user (such as sweat), rainfall, and the like may infiltrate into the inside of the housing part 102 to damage the circuit components constituting the electric part 101 and deteriorate the adhesiveness of the adhering part 103 present in a further lower layer thereof.

The electric part 101 includes the sound pickup sensor, the control part, the power source part, and the like, and the substrate having these circuit components mounted thereon (described above). It is preferred that the substrate constituting the electric part 101 have flexibility and stretchability to follow the variation of the surface of the body (a free curved surface) of the user to which the main body of the information processing apparatus 100 adheres. The flexibility and stretchability are enhanced by, for example, using a flexible substrate and forming slits in the flexible substrate in the directions for two or more axes, and the substrate tends to follow the free curved face. In contrast, when the substrate has no flexibility and no stretchability, the main body of the information processing apparatus 100 tends to be peeled off from the surface of the body of the user to which the main body adheres.

The adhering part 103 has a sheet-like shape and the surface thereof is a paste face having adhesion performance, and the adhering part 103 adheres to the surface of the body of the user to be able to fix the main body of the information processing apparatus 100 to the body of the user. Moreover, taking into consideration that a significant amount of body fluid (such as sweat) are secreted or discharged from the skin of the user, it is preferred that the adhering part 103 have moisture permeability (or water permeability, or liquid permeability). The adhering part 103 is constituted using, for example, a porous material having one or more apertures.

It is preferred that the paste face of the adhering part 103 be formed by an adhesive material applicable to the skin (such as, for example, the one not stimulating the skin and avoiding generation of any allergy). Moreover, it is preferred that, in the state where the paste face of the adhering part 103 is unused, the paste face be protected by a release paper sheet (not depicted) such that the adhesion performance can be maintained avoiding adhesion of any foreign particle and the like to the paste face. Additionally, the information processing apparatus 100 may be configured to transition to its use state to have the power source thereof turned on, by the fact that the release paper sheet is peeled off from the adhering part 103.

The body fluid processing part 104 processes the body fluid of the user infiltrating through the aperture of the adhering part 103 to thereby block the body fluid such that the body fluid does not reach the electric part 101. The body fluid processing part 104 is constituted using a mesh material such as, for example, a high-molecule polymer moisture absorbing material. The body fluid processing part 104 guides the body fluid using the capillary activity and releases the body fluid into the environment (the outside of the information processing apparatus 100). It is preferred that the body fluid processing part 104 be configured as a replaceable piece.

Figure 2:
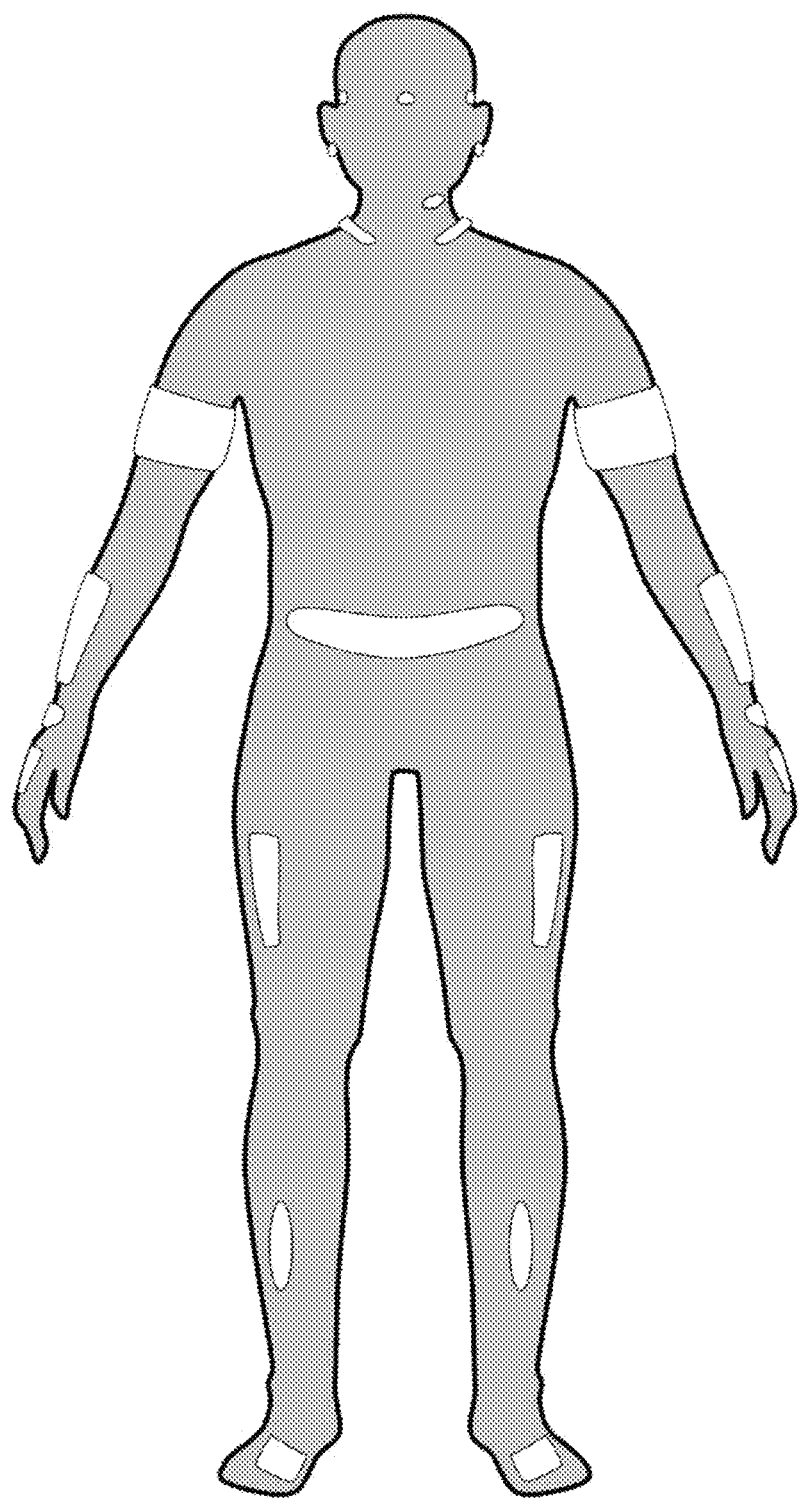
FIG. 2 is a diagram exemplifying points to which the information processing apparatus proposed herein can adhere.

In addition, in FIG. 1, the information processing apparatus 100 adhering to the region beneath the jaw of the user is exemplified while it is assumed that the main body of the information processing apparatus 100 is used by being adhered to each of various points on the surface of the body of the user. FIG. 2 exemplifies the regions on the body of the user for each of which it is assumed that the information processing apparatus proposed herein adheres. It is assumed that, as depicted, the information processing apparatus is used as a what-is-called wearable device being caused to adhere to each of the regions such as a temple, the glabella, the back of an ear, a region beneath the jaw, the neck, the root of the neck, the throat portion, an upper arm, a forearm, wrist, the back of a hand, and the abdomen. In addition, though not depicted, a similar information processing apparatus can be used as an IoT device by causing this information processing apparatus to adhere to not the human body but each of various machines and articles.

Figure 4:
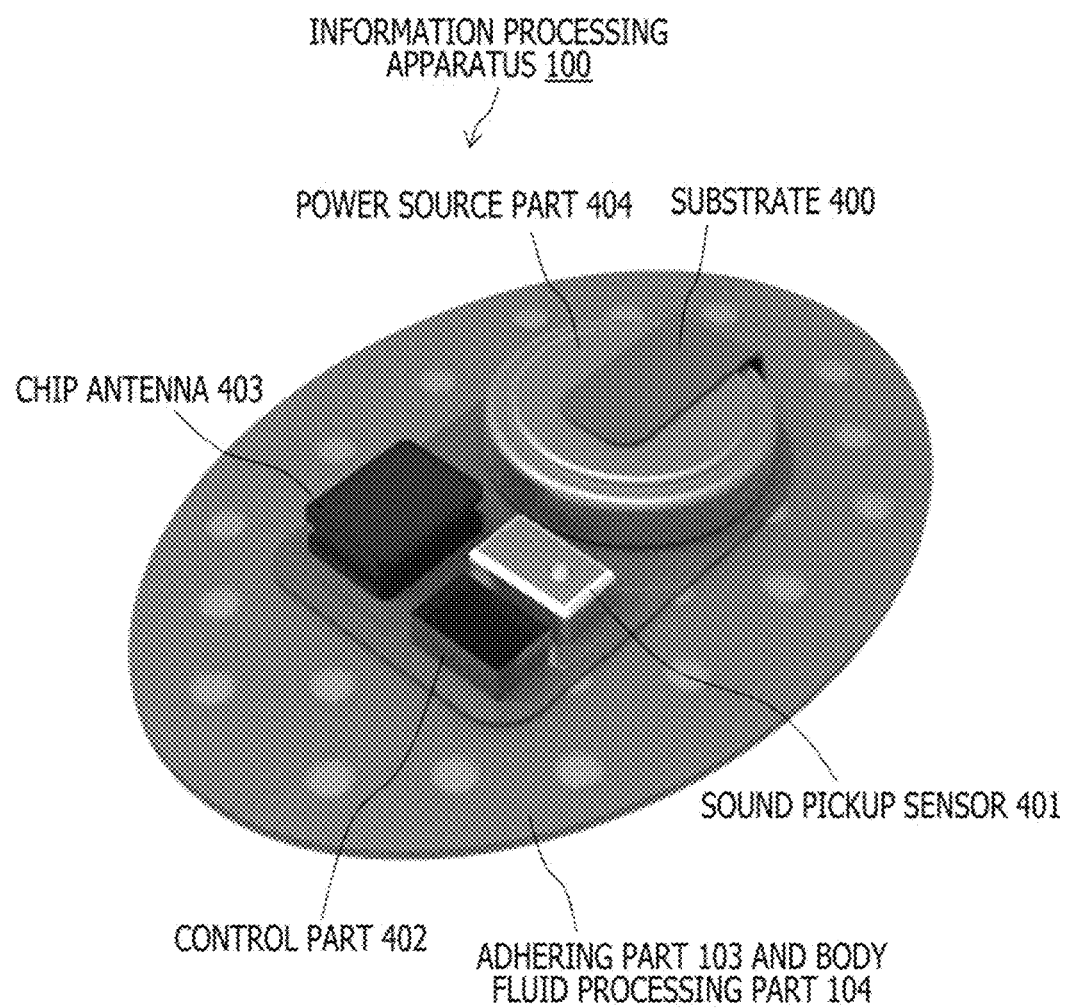
FIG. 4 is a diagram exemplifying an image of actual installation of an electric part 101 on a substrate 400.

FIG. 4 exemplifies an image of actual mounting of the electric part 101 to a substrate. On the substrate 400 having the flexibility and the stretchability, a power source part 404 including a coin battery is mounted together with the circuit parts such as a sound pickup sensor 401, a control part 402 acting also as a communication processing part, and a chip antenna 403.

Figure 3:
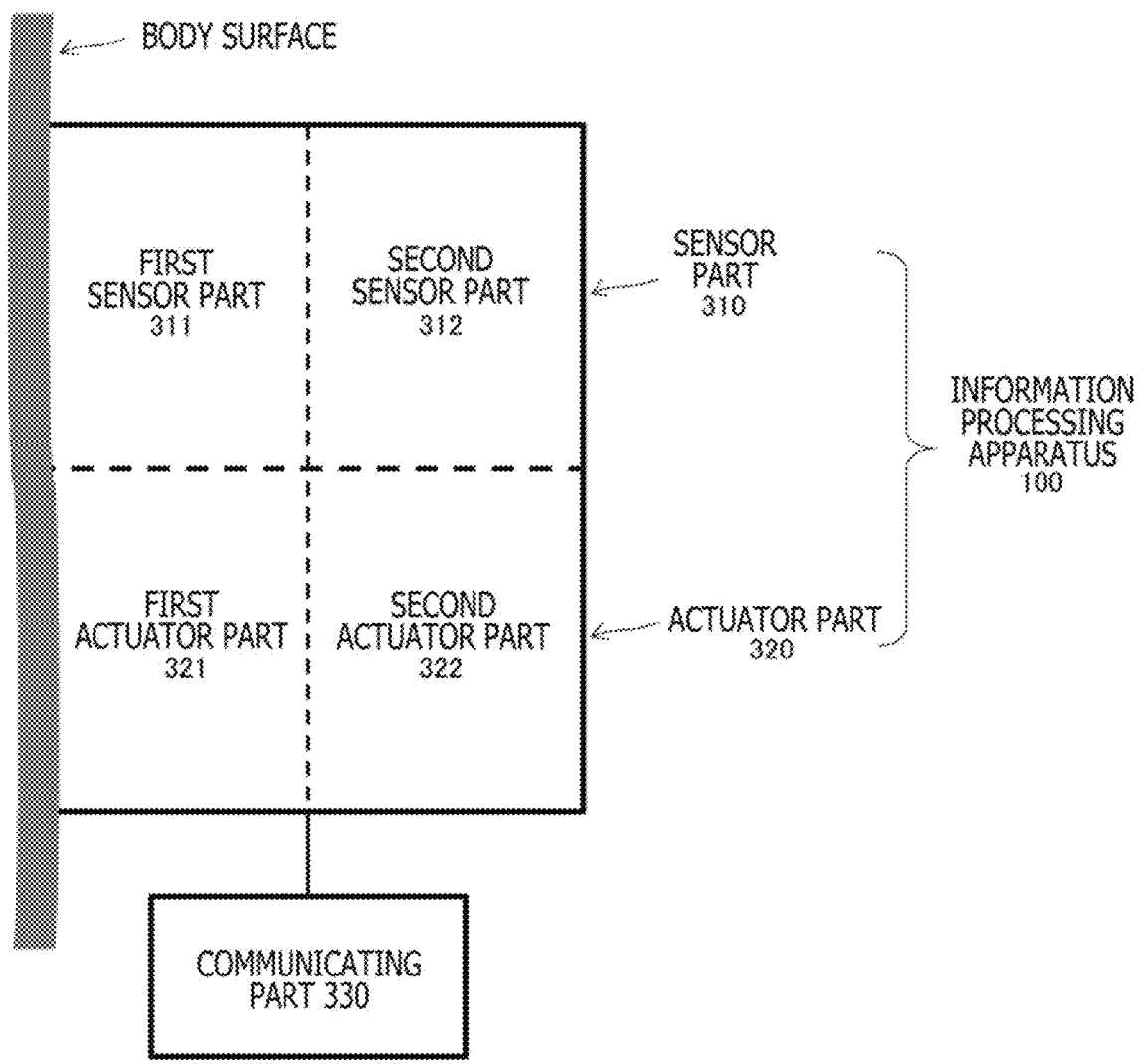
FIG. 3 is a diagram schematically depicting an exemplary configuration of an input and output function of the information processing apparatus 100 that is used by being adhered to the body surface of a user.

FIG. 3 schematically depicts an exemplary configuration of an input and output function of the information processing apparatus 100 that is used by being adhered to the surface of the body of the user. The depicted information processing apparatus 100 includes a sensor part 310, an actuator part 320, and a communicating part 330.

Utilizing the feature that the main body of the information processing apparatus 100 is in contact with the surface of the body of the user, the sensor part 310 includes a first sensor part 311 that detects information relating to the user (the human body), and a second sensor part 312 that detects information relating to the outside (the external world) of the user. Moreover, the actuator part 320 includes a first actuator part 321 that outputs information to the user (the human body), and a second actuator part 322 that outputs information to the outside (the external world and the people around) of the user.

As the basic function of the information processing apparatus 100, the control part (not depicted in FIG. 3) drives at least one of the first actuator part 321 or the second actuator part 322, on the basis of the results of the detection by at least one sensor of the sound pickup sensor, the first sensor part 311, or the second sensor part 312. The result of detection by the sensors (such as, for example, the biological information of the user him/herself or the environment information relating to the surroundings) can be notified of to the user by driving the first actuator part 321. Moreover, the result of detection by the sensors can be delivered to the surroundings of the user by driving the second actuator 322.

Moreover, as the function included in the information processing apparatus 100, the control part sends out the result of the detection by the sensor part 310 from the communicating part 330 to the outside, or drives the actuator part 320 on the basis of the result of the detection by the sensor part 310.

Moreover, as yet another function included in the information processing apparatus 100, the control part controls the driving of the actuator 320, controls the detection process by the sensor part 310, and the like on the basis of the information received from the outside through the communicating part 330.

In addition, the control part may include a memory to store therein an individual identification number to identify the information processing apparatus 100 (or the user), an encryption key to be used to prevent any eavesdropping during information exchange with the outside, and the like.

From the viewpoint that the sound pickup sensor picks up the sound produced by the user having the information processing apparatus 100 adhering thereto, the above sound pickup sensor can be included in the first sensor part 311. The sound pickup sensor may be understood as an essential component of the information processing apparatus 100, that is surely not included in the first sensor part 311. The sound pickup sensor picks up the sound produced by the user, using the air conduction from the mouth, the flesh conduction or the bone conduction in the head. It is preferred that a sound pickup hole to pick up an air-electrically driven sound is bored in the housing part 102. Moreover, it is preferred that a waterproof process be applied to the sound pickup hole.

Moreover, the first sensor part 311 can include various types of biological sensors that each can detect biological information such as a brain wave sensor, a vein sensor, a myoelectric sensor, a body temperature sensor, a perspiration sensor, a heart rate or pulse sensor, and a line-of-sight sensor.

For example, in the case where the information processing apparatus 100 adheres is used by being adhered to a point close to the mouth or the vocal cords such as a region beneath the jaw, the neck, the root of the neck, and the throat portion, the sound pickup sensor can pick up any minute sound information including those through the air conduction from the mouth, and the flesh conduction and the bone conduction in the head. Moreover, even in the environment having any noise present therein, the voice of the user can be separated to be picked up using the flesh conduction and the bone conduction.

Figure 5:
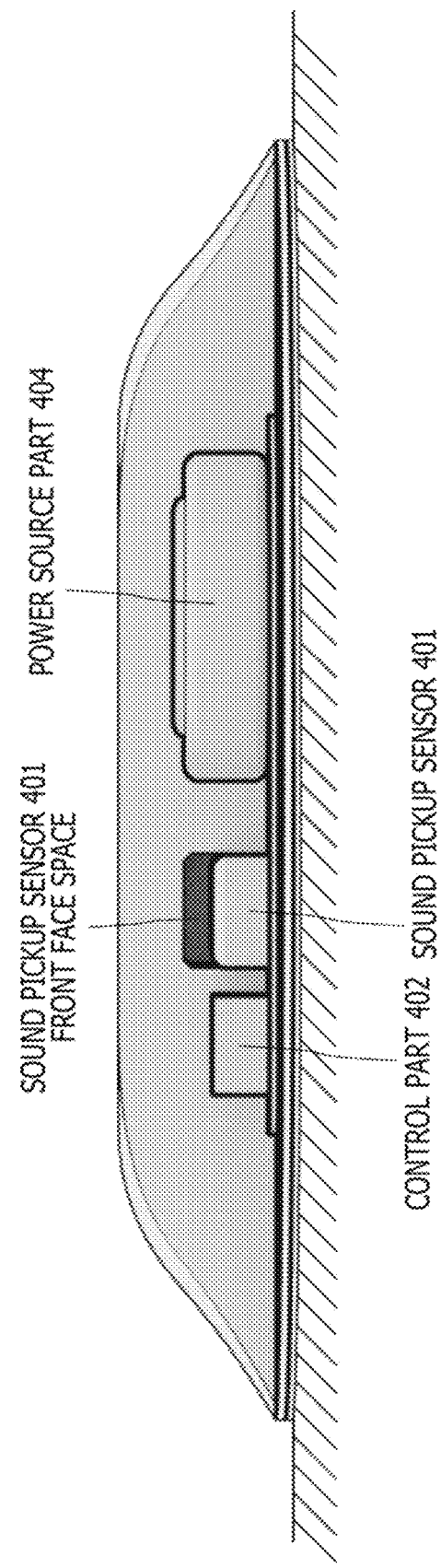
FIG. 5 is a diagram exemplifying a cross-sectional configuration of the information processing apparatus 100 in the state where the information processing apparatus 100 adheres to the body surface a user.
Figure 6:
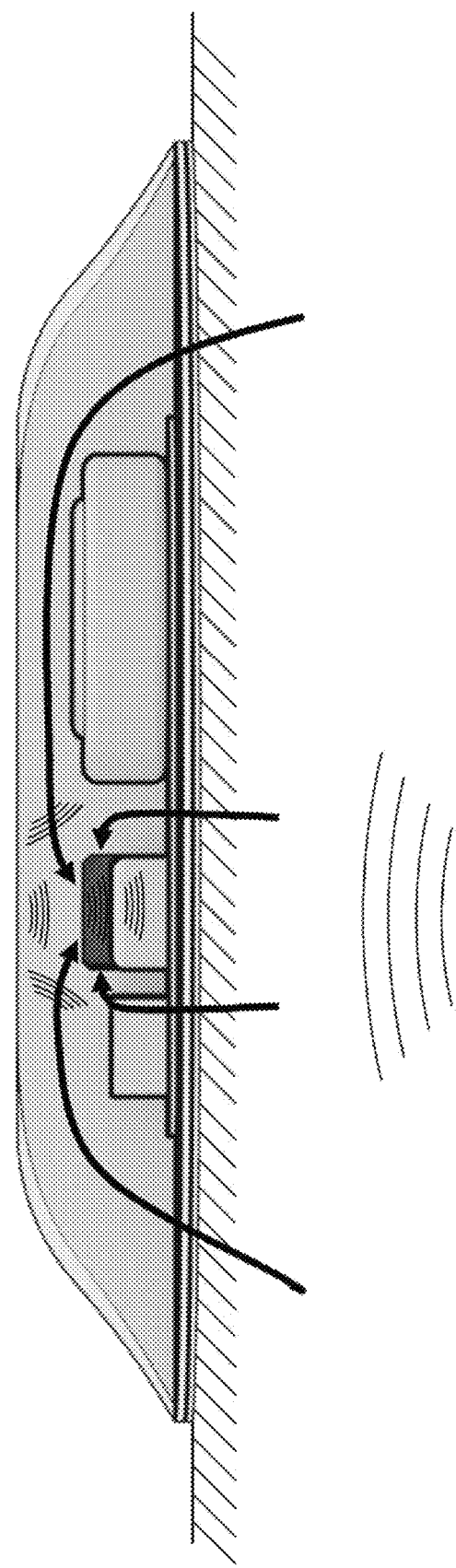
FIG. 6 is a diagram exemplifying the state where a sound pickup sensor 401 picks up a voice of a user.

FIG. 5 exemplifies a cross-sectional configuration of the information processing apparatus 100 in the state where the information processing apparatus 100 adheres to the surface of the body of the user. As has been already described with reference to FIG. 4, on the substrate 400 having the flexibility and the stretchability, the circuit pieces such as the sound pickup sensor 401, the control part 402 acting also as the communication processing part, and the power source part 404 including a coin battery are mounted. Moreover, FIG. 6 exemplifies the state where the sound pickup sensor 401 picks up the voice of the user. It is however assumed in FIG. 6 that the information processing apparatus 100 adheres to the throat portion of the user. When the voice produced by the user conducts through the flesh and the skin to reach the main body of the information processing apparatus 100, the voice further propagates in the air as indicated by arrows in FIG. 6 to vibrate the air in the front face space of the sound pickup sensor 401. The diaphragm (not depicted) in the sound pickup sensor is vibrated by the air vibration and the voice of the user can thereby be effectively picked up.

The information processing apparatus 100 may record the acoustic data picked up by the sound pickup sensor as an audio log, and may further transmit the audio log to an external apparatus through the communicating part 330. Moreover, in the case where the information processing apparatus 100 includes an biological sensor as the first sensor 311, the audio data picked up by the sound pickup sensor and the biological information detected by the biological sensor may be synchronized with each other in the temporal direction, to be recorded, to be transmitted to an external apparatus, or the like.

The data amount however becomes huge when the audio log is always recorded, and the control part may therefore execute filtering for the audio logs (or intermittent recording of the audio data) on the basis of the biological information acquired from the biological sensor (above described). During the reproduction, the audio log may intermittently be reproduced by filtering on the basis of the biological information synchronized with the audio log in the temporal direction. For example, effective and efficient viewing and listening of the past experience of the user are enabled by filtering the audio log using the precisely detected heart rate. Moreover, on the basis of brain wave data and the like, the recording and external outputting of the audio log may be executed in a time period limited to that in which the user is assumed to be in the awake state or in which the user indicates an interest.

Additionally, the information processing apparatus 100 can also be used as a sound collector or a hearing aid by executing sound picking up to amplification to reproduction by the cooperative operation by the sound pickup sensor included in the first sensor part 311 and the speaker (described later) included in the first actuator part 321.

Moreover, in the case where the information processing apparatus 100 is used by being adhered to the head such as a temple or the glabella, the brain wave can highly precisely be detected using the brain wave sensor. The control part analyzes the result of the detection by the brain wave sensor to recognize the intention and the emotion of the user, and a brain interface can thereby be realized. Moreover, when the control part senses any drowsiness of the user on the basis of the result of the detection by the brain wave sensor, the control part can also execute, for example, an operation of repulsing the drowsiness using electric stunning by driving the first actuator part 321.

Moreover, a vibration sensor can be included in the first sensor part 311. The vibration sensor includes, for example, an acceleration sensor, a gyro sensor, or a geomagnetism sensor, or a combination of two or more sensor elements of these. On the basis of the result of the detection by the vibration sensor, the control part can detect the posture and the body motion (such as an impact, a vibration, an inclination, tumbling, falling, moving, and the like) of the user having the information processing apparatus 100 adhering thereto on its body. Moreover, in the case such as that where the information processing apparatus 100 is used by being adhered to the back of a hand or a finger of the user, the control part can analyze the result of the detection by the vibration sensor and can thereby detect a gesture performed by the user.

Furthermore, the control part can extract characteristic data from vibration data detected by the vibration sensor and can recognize the action of the user on the basis of the temporal sequence of the characteristic data accumulated in a predetermined amount (see, e.g., PTL 3). Moreover, the control part may sequentially learn the temporal sequence information of the characteristic data. The vibration data acquired from the vibration sensor has a different characteristic for each of the points to which the main body of the information processing apparatus 100 adheres. The control part therefore can also further estimate the point to which the main body of the information processing apparatus 100 adheres on the basis of the vibration data acquired from the vibration sensor (or the temporal sequence of the characteristic data extracted from the vibration data).

Moreover, an adhesion sensor detecting whether or not the adhesion state is established where the main body of the information processing apparatus 100 adheres to the body of the user can also be included in the first sensor part 311. As to the adhesion sensor, the adhesion sensor can be constituted using, for example, a capacitance sensor that detects any variation of the capacitance associated with the approach of the human body, an infrared reflection sensor that detects a reflected light beam of an infrared light beam applied to the surface (the skin) of the human body, and the like. In response to the adhesion state, the control part may control the startup (the recovery from the standby state) of the information processing apparatus 100 and the startup of the predetermined processes such as the authentication.

Suitableness or unsuitableness is however present for the detection of the biological information depending on the point to which the main body of the information processing apparatus 100 adheres and, moreover, necessity and unnecessity differ in the biological information depending on the use of the information processing apparatus 100 itself. Any properly necessary biological sensor only has to be incorporated in the first sensor part 311 in accordance with the necessity or unnecessity of the adhesion point and the biological information.

Examples of the second sensor part 312 include a sound pickup sensor (such as a microphone) that picks up (not the real voice of the user but) a sound or a noise in the outer world, an image sensor that images the scenery of the surroundings, and an environment sensor that detects the external environment information such as the temperature, the humidity, the luminance, and the atmospheric pressure. Moreover, from the view point that the chip antenna 403 (described above) detects the radio wave (a wireless signal), the chip antenna 403 can also be included in the second sensor part 312 in the broad sense.

Moreover, a position information sensor such as a GPS (Global Positioning System) sensor can be included in the second sensor part 312. The information processing apparatus 100 can however include a position detection function using a means other than the position information sensor. For example, in the case where an image sensor is included as the second sensor part 312, self-location estimation can be realized utilizing the SLAM (Simultaneous Localization and Mapping) technique. Moreover, the current location can be calculated on the basis of the balance of the radio wave intensities from the surrounding plural access points that are received by the chip antenna 403, using the PlaceEngine technique.

In the case where the position information sensor is included as the second sensor part 312 or the information processing apparatus 100 has a position detection function, the control part can recognize the action of the user on the basis of the temporal sequence of the position information, that is, path information of the user.

Suitableness or unsuitableness for the detection of the outer environment information is present depending on the point to which the main body of the information processing apparatus 100 adheres. For example, in the case where the main body of the information processing apparatus 100 adheres to the glabella of the user as depicted in FIG. 1, this is suitable for imaging the scenery of the surroundings while, in the case where the main body adheres to the region beneath the jaw, this is unsuitable for imaging the scenery of the surroundings. The second sensor part 312 therefore only has to incorporate therein a properly necessary environment sensor in accordance with the necessity or unnecessity of the adhesion point and the biological information.

The first actuator part 321 basically outputs directly to the body of the user. Examples of the first actuator part 321 include, for example, a small speaker, a flesh conduction speaker that outputs a sound using the flesh conduction, a haptic device capable of haptic-outputting, a vibration actuator that applies stimulation using a vibration, an actuator that provides weak electric stunning (or a device that outputs a micro current). Suitableness or unsuitableness of the outputting is however present depending on the point to which the main body of the information processing apparatus 100 adheres and, moreover, necessity and unnecessity of the outputting differ depending on the use of the information processing apparatus 100 itself. Any properly necessary actuator element only has to be incorporated in the first sensor part 321 in accordance with the necessity or unnecessity of the adhesion point and the information outputting.

The second actuator part 322 basically outputs information to the user having the information processing apparatus 100 adhering thereto and the people around the user. Examples of the information output from the second actuator part 322 include externally provided information that is received through the communicating part 330. Moreover, the results of detection by the first sensor part 311 and the second sensor part 312 and the result of analysis or recognition of the detected data thereof by the control part can also be output from the second actuator part 322.

Examples of the second actuator part 322 include a displaying part that outputs a light beam or an image, a speaker that outputs a sound, and the like. The displaying part can be constituted using, for example, a highly flexible organic EL (electro luminescence) display. The displaying part is not accommodated in the housing 102 and is disposed on the surface of the housing 102. Moreover, in the case where the speaker is included as the second actuator part 322, a sound output hole and an air discharge hole may be formed in the surface of the housing 102.

Suitableness or unsuitableness of the outputting is however present depending on the point to which the main body of the information processing apparatus 100 adheres and, moreover, necessity and unnecessity of outputting differ depending on the use of the information processing apparatus 100 itself. Any properly necessary actuator element only has to be incorporated in the second actuator part 322 in accordance with the necessity or unnecessity of the adhesion point and the information outputting.

The communicating part 330 executes information communication with the outside. For example, the communicating part 330 outputs the result of the detection by the sensor part 310 processed by the control part to the outside. Moreover, the communicating part 330 inputs instructions for the control part and the actuator part 320, from the outside.

The communicating part 330 executes communication with an apparatus (such as a cloud) on the Internet through wireless communication such as, for example, Wi-Fi. Otherwise, the communicating part 330 executes communication with another information terminal held by the user such as a smartphone using Bluetooth (a registered trademark) or another short-distance communication function. When the communicating part 330 executes information communication with an external apparatus wirelessly, it is preferred that secret communication be executed using an encryption key (described above) to prevent any eavesdropping.

Moreover, the communicating part 330 may execute communication with an information terminal at a very short distance and the authentication process using a proximity wireless communication technique like NFC (near field communication). Moreover, the communicating part 300 may have a human body communication function and may execute information communication with another information processing apparatus adhering to another region of the body of the same user and an information terminal held by the same user through the human body communication.

The sensor elements applicable to the first sensor part 311 and the second sensor part 312, and the actuator elements applicable to the first actuator part 321 and the second actuator part 322 depend also on the point to which the main body of the information processing apparatus 100 adheres. Suitableness and unsuitableness of the sensor elements and the actuator elements in accordance with the adhesion point are listed in FIG. 7.

Such methods can be considered as the configuration method for the information processing apparatus 100 for only the minimal sensor elements and the actuator elements to be included therein limiting the point for the adhesion, and a high-specification configuration method for the information processing apparatus 100 for as many types of sensor element and actuator element as possible to be included therein assuming that the information processing apparatus 100 is applied to each of many adhesion points.

According to the former method, one information processing apparatus 100 can relatively inexpensively be manufactured and the information processing apparatus 100 can therefore be also set to be a disposable-type information processing apparatus 100.

Moreover, according to the latter configuration method, the sensor elements and the actuator elements that do not need to operate are present depending on the point for the actual adhesion. Turning on and off of each of the sensor elements and the actuator elements may therefore be set so as to be manually switchable therebetween, or the control part may estimate the adhesion point on the basis of the vibration data acquired from the vibration sensor (the body motion of the user) and the sensor data of the biological sensor and the like to automatically execute the switching control of the turning on and off therebetween. Moreover, control that does not control the complete switching of turning on and off of each of the sensor elements and the actuator elements but that switches the sensor sensitivity stepwise or that switches the output level of the actuator stepwise in accordance with the intended use estimated from the point for the adhesion, or the like may be executed.

In addition, a patch material for the skin that incorporates therein a temperature sensor and that is used by being adhered to the skin of a specimen material such as a human body has already been proposed (see, e.g., PTL 2). The patch material for the skin also incorporates therein an electric part such as a microprocessor and a transmitter, and a button-type battery in addition to the temperature sensor but does not include any sound pickup sensor. In other words, from the viewpoint that the patch material for the skin cannot use any sound information for UI and cannot handle any audio log, this patch material essentially differs from the information processing apparatus disclosed herein.

Example 1

A first Example assumes that the information processing apparatus 100 (see FIG. 1) is caused to adhere to the region beneath the jaw (or the throat portion) of the user.

Because the information processing apparatus 100 is used by being adhered to a point close to the mouth or the vocal cords, the sound pickup sensor can pick up minute sound information as the life log information. Moreover, even in an environment with a noise, the sound pickup sensor can separate the user's voice from the noise using the flesh conduction and the bone conduction and can thereby efficiently pick up the user's voice (see, FIG. 6). Moreover, because the information processing apparatus 100 adheres to the region beneath the jaw and is inconspicuous, the sound pickup sensor can record the audio log without being noticed by the user him/herself and the dialogue counterpart of the user.

Example 2

A second Example also assumes that the information processing apparatus 100 (see FIG. 1) is caused to adhere to the region beneath the jaw or the throat portion of the user. Moreover, it is assumed that the information processing apparatus 100 includes at least one biological sensor in addition to the sound pickup sensor, as the first sensor 311.

The biological sensor includes at least one of a brain wave sensor, a vein sensor, a myoelectric sensor, a body temperature sensor, a perspiration sensor, a heart rate or pulse sensor, a vibration sensor, or the like, or a combination of two or more of these sensors. The biological sensor detects the biological information of the user having the main body of the information processing apparatus 100 adhering to the surface of the body thereof.

Similar to the first Example, in this Example, because the information processing apparatus 100 also adheres to the region beneath the jaw and is inconspicuous, the information processing apparatus 100 record the audio log without being noticed by the user him/herself and the dialogue counterpart of the user. Moreover, the recorded or the live audio data may also be transmitted to an external apparatus through the communicating part 330.

Moreover, in this Example, because the information processing apparatus 100 includes the biological sensor as the first sensor 311, the information processing apparatus 100 may synchronize the audio data picked up by the sound pickup sensor and the biological information detected by the biological sensor with each other in the temporal direction to record these, or may transmit the audio data to an external apparatus establishing its synchronization with the biological information in the temporal direction. In this case, the audio data and the biological information can collectively be managed as a life log of the user.

When the audio log is always recorded, a problem however arises that the data amount becomes huge. The control part therefore executes filtering for the audio log on the basis of the biological information acquired from the biological sensor (described above).

For example, when the information processing apparatus 100 reproduces the audio data, the information processing apparatus 100 may execute the filtering on the basis of the biological information whose synchronization with the audio log in the temporal direction is established, to thereby intermittently reproduce the audio log. For example, the degree of tension of the user and the like can be estimated using the heart rate. The past experience of the user can therefore be efficiently and effectively viewed and listened to by filtering the audio log using the precisely detected heart rate.

Moreover, in the case where the main body of the information processing apparatus 100 adheres to the region with which the brain wave can be detected with a low noise such as not the region beneath the jaw but the head, the information processing apparatus 100 may execute the recording and external outputting of the audio log limiting the time period to that in which it is estimated that the user is in the awake state on the basis of the brain wave data.

In addition, the method of establishing the synchronization of the audio log and the biological information with each other in the temporal direction is optional. For example, the audio data and the biological information synchronized with each other may be consolidated with each other, or a time stamp may be attached to each of the audio data and the biological information each handled separately from each other.

Figure 8:
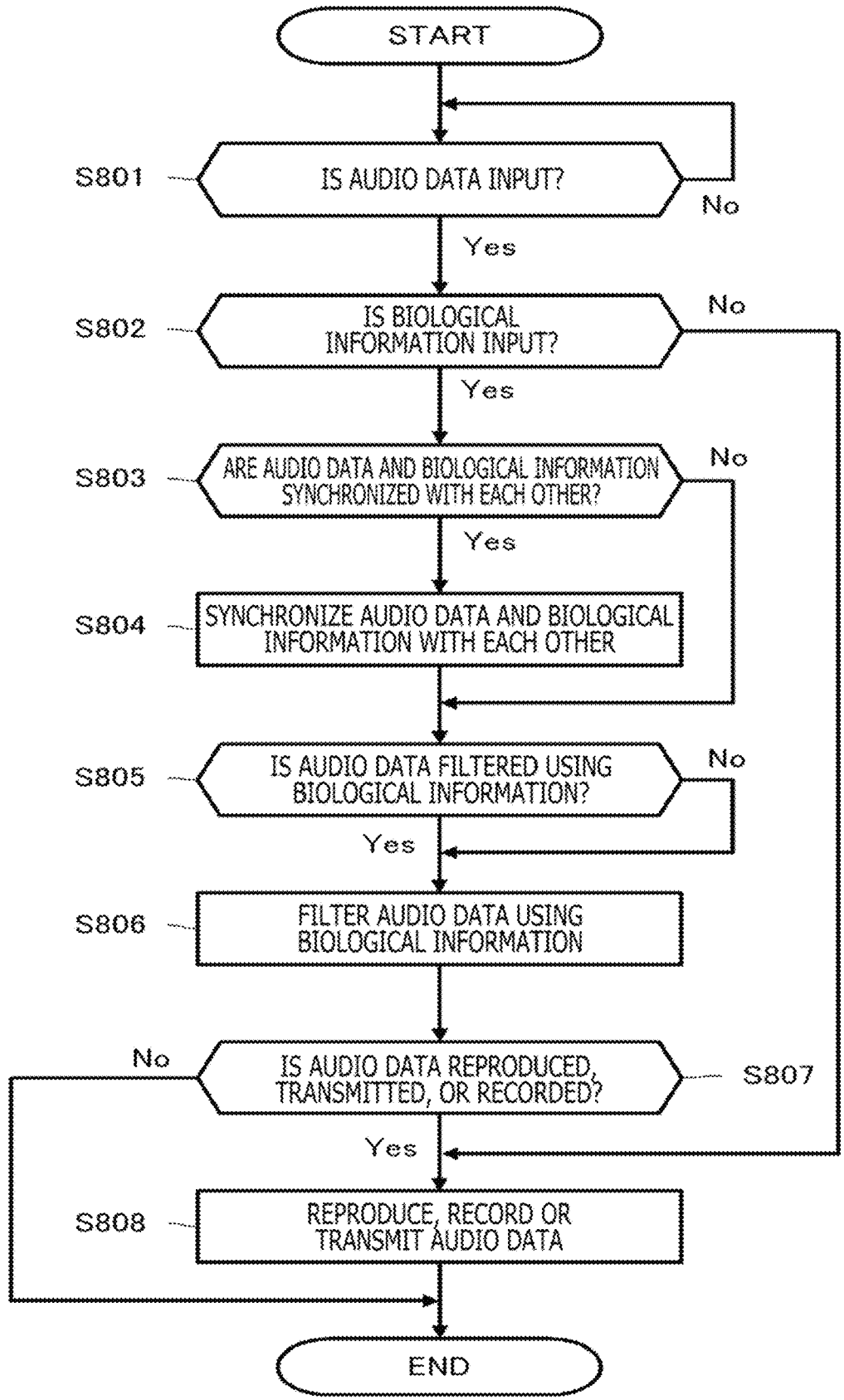
FIG. 8 is a flowchart depicting a process procedure for the information processing apparatus 100 to associate audio data picked up by the sound pickup sensor with biological information and record or transmit the audio data to the outside.

FIG. 8 depicts, in the form of a flowchart, a process procedure for the information processing apparatus 100 to record therein by correlating the audio data with the biological information or transmit the audio data picked up by the sound pickup sensor to the outside. It is assumed that the depicted process procedure is executed led by, for example, the control part in the information processing apparatus 100.

In the case where an input of a sound is present for the sound pickup sensor (Yes of step S801), the control part next further checks whether or not any biological information is detected by the biological information (step S802).

Concerning the above, in the case where no biological information is detected by the biological sensor (No of step S802), the control part executes reproduction and outputting from the second actuator part 322, transmission to the outside, or recording for the audio data picked up by the sound pickup sensor in accordance with the transmission condition or the recording condition for those except the biological information (step S808).

Moreover, in the case where any biological information is detected by the biological sensor (Yes of step S802), the control part checks whether or not the audio data and the biological information are synchronized with each other in the temporal direction (step S803). In the case where the audio data and the biological information are synchronized with each other in the temporal direction (Yes of step S803), the control part synchronizes the biological information with the audio data in the temporal direction (step S804).

The control part next checks whether or not the picked up audio data is filtered using the biological information (step S805).

In the case where it is determined that the audio data needs to be filtered using the biological information (Yes of step S805), the control part filters the picked up audio data on the basis of the biological information (step S806).

The control part next reproduces and outputs the picked up audio data (for which the case is present where the audio data is synchronized with the biological information in the temporal direction or where the audio data is filtered on the basis of the biological information) using the second actuator part 322, and transmits the audio data through the communicating part 330 or checks whether or not the audio data is recorded as an audio log (step S807).

At step S807, the control part determines necessity or unnecessity of the reproduction and outputting, the external outputting, and the recording of the audio data, on the basis of a sound instruction from the user, the recognition result for the biological information, an external instruction received through the communicating part 330, and the like.

In the case where the determination result acquired at step S807 is affirmative, the control part thereafter executes the reproduction and outputting from the second actuator part 322, the transmission to the outside, or the recording of the audio data picked up by the sound pickup sensor (step S808).

Example 3

In a third Example, the point to which the main body of the information processing apparatus 100 adheres is not especially limited while it is assumed that the information processing apparatus 100 includes the adhesion sensor that detects whether or not the adhesion state is established where the main body of the information processing apparatus 100 adheres to the body of the user.

As to the adhesion sensor, the adhesion sensor can be constitute using, for example, a capacitance sensor that detects any variation of the capacitance associated with the approach of the human body, an infrared reflection sensor that detects any reflected light beam of an infrared light beam applied to the surface (the skin) of the human body, and the like. It is preferred that the adhesion sensor have a configuration adapted to the point to which the main body of the information processing apparatus 100 is caused to adhere. In addition, the adhesion state can be estimated using the determination as to whether or not the state where the biological signal (such as the heart beats) can be detected by the biological sensor is established. Moreover, relating also to a sixth Example described later, the point for the adhesion can also be simultaneously estimated together with the adhesion state of the main body of the information processing apparatus 100 for the body of the user, on the basis of the vibration data acquired from the vibration sensor.

The control part controls the operation of the information processing apparatus 100 in accordance with the adhesion state. The state where the main body of the information processing apparatus 100 does not adhere to the surface of the body of the user can basically be regarded as the state where the information processing apparatus 100 is not used. The control part may therefore cause the circuits except some functions including the adhesion sensor to transition into a standby state or a stoppage state to facilitate reduction of the power consumption when the non-adhesion state is detected by the adhesion sensor.

On the other hand, when the adhesion state for the body of the user is detected by the adhesion sensor, the control part starts up the circuits that are each in the standby state or the stoppage state. Moreover, the control part may start up the predetermined processes such as the authentication process in response to the fact that the adhesion state for the body of the user is detected by the adhesion sensor.

It is assumed that the "authentication" as used herein includes either one process or both processes of the authentication for the user him/herself having the main body of the information processing apparatus 100 adhering thereto, and authentication for another device. Moreover, the control part may execute pairing with another device in the authentication process. For the former user authentication, for example, the biological information detected by the biological sensor may be used. Moreover, to realize the authentication process without any fraud, the electric part 101 may include circuit pieces each having tamper resistance such as an IC chip.

Figure 9:
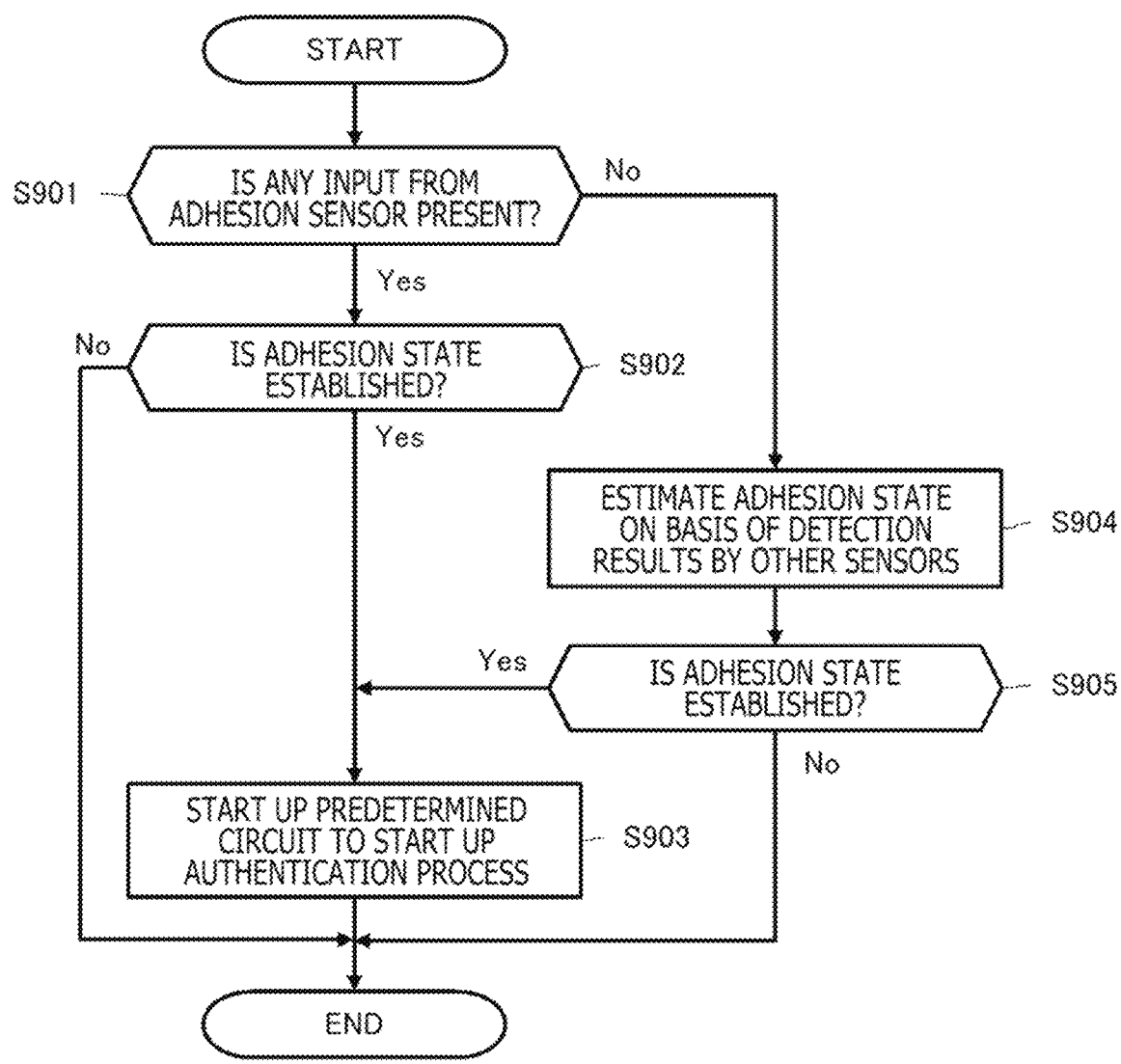
FIG. 9 is a flowchart depicting a process procedure to cause the information processing apparatus 100 to operate in accordance with the adhesion state to the body of a user.

FIG. 9 depicts, in the form of a flowchart, a process procedure to cause the information processing apparatus 100 to operate in accordance with the adhesion state for the body of the user. It is assumed that the depicted process procedure is executed led by, for example, the control part in the information processing apparatus 100. In addition, hereinafter, for convenience, the description will be made assuming that the adhesion sensor outputs a detection signal when the adhesion state varies (when the state transitions from the adhesion state to the non-adhesion state or when the state transitions from the non-adhesion state to the adhesion state).

The control part first checks whether or not any input from the adhesion sensor is present (step S901).

When an input from the adhesion sensor is present (Yes of step S901), the control part further checks whether or not the information processing apparatus 100 transitions into the adhesion state (step S902).

Moreover, when no input from the adhesion sensor is present (No of step S901), the control part tries determining the adhesion state on the basis of the results of the detection of the sensors other than the adhesion sensor (such as, for example, the biological sensor and the vibration sensor) (step S904).

When it turns out next that the main body of the information processing apparatus 100 is in the where the main body adheres to the body of the user (Yes of step S902) or when it is estimated that the main body is in the adhesion state (Yes of step S905), the control part starts up the circuits each in the standby state or the stoppage state or starts up the authentication process (step S903), and causes this process to come to an end.

On the other hand, when it turns out that the main body of the information processing apparatus 100 is not in the state where the main body does not adhere to the body of the user (No of step S902) or when it is estimated that the main body is not in the adhesion state (No of step S905), the control part does not execute the starting up of the circuits and the starting up of the authentication process, and causes this process to come to an end.

Example 4

A fourth Example assumes that the main body of the information processing apparatus 100 is caused to adhere to the region close to an ear such as the back of the ear and the information processing apparatus 100 includes a speaker as the second actuator. The information processing apparatus 100 can therefore provide a sound agent function to the user using the speaker.

In the case where the information processing apparatus 100 includes the vibration sensor as the second sensor part 312, the control part can recognize the action of the user on the basis of the temporal sequence of the detected vibration data. Moreover, in the case where the information processing apparatus 100 includes the position information sensor as the second sensor part 312 or has the position detection function, the control part can recognize the action of the user on the basis of the path information of the user. The control part can next provide the sound agent that matches with the situation having the user present therein on the basis of the recognition result for the action.

The control part controls the driving of the sound agent on the basis of the recognition result for the sound of the user picked up by the sound pickup sensor, the position information relating to the user that varies moment by moment, and the recognition result for the action. Otherwise, the control part may acquire information relating to a POI (point of interest) estimated on the basis of the current position of the user from an external apparatus (such as a cloud) through the communicating part 330 to present this information to the user through the sound agent.

Moreover, the control part may control the driving of the sound agent on the basis of data received from an external apparatus (an information terminal such as a smartphone, a cloud, or the like) through the communicating part 330. When the control part acquires the information for the sound agent, the control part may transmit information such as the position information relating to the user and the action recognition result to the external apparatus through the communicating part 330.

Moreover, the main body of the information processing apparatus 100 may be caused to adhere to a region that tends to be seen by the user such as the back of a hand, and the information processing apparatus 100 may include a displaying part as the second actuator. The displaying part is not accommodated in the housing 102 but is disposed on the surface of the housing 102, and the user can thereby view and listen to the display screen. The main body of the information processing apparatus 100 can be caused to adhere following the curved face of the back of a hand or the like with excellent feeling of fitting by constituting the displaying part using a highly flexible organic EL display.

In the case where the information processing apparatus 100 includes the vibration sensor as the second sensor part 312, the control part can recognize the action of the user on the basis of the temporal sequence of the detected vibration data. Moreover, in the case where the information processing apparatus 100 includes the position information sensor as the second sensor part 312 or has the position detection function, the information processing apparatus 100 can recognize the action of the user on the basis of the path information for the user. The control part can next present visual guide information that matches with the situation having the user present therein, on the displaying part on the basis of the recognition result for the sound of the user picked up by the sound pickup sensor or the recognition result for the action of the user.

Moreover, the control part may transmit information relating to the recognition result for the sound of the user and the recognition result for the action of the user to an external apparatus through the communicating part 330 to display on the displaying part the related information acquired from the external apparatus. The information processing apparatus 100 surely may also receive the information irrelevant to the sound command and the action of the user, from the external apparatus to display this information on the displaying part.

Moreover, the information processing apparatus 100 according to the fourth Example may include both of the speaker and the displaying part to reproduce and output a video image and sound information received from an external apparatus through the communicating part 330.

Example 5

A fifth Example assumes that two of an information processing apparatus 100-1 and an information processing apparatus 100-2 that are caused to concurrently adhere to the body of the same user operate in cooperation with each other. The one information processing apparatus 100-1 includes an imaging function such as a camera (or an image sensor) or the like, and the other information processing apparatus 100-2 includes a displaying part or a display function, and displays and outputs the video image imaged by the information processing apparatus 100-1 in, for example, real time.

The point to which the information processing apparatus 100-1 including the imaging function is caused to adhere is optional. The other information processing apparatus 100-2 however displays the point that is in the blind angle for the user when the information processing apparatus 100-1 is caused to adhere to a point with which the line of sight of the camera is set to be in the direction of the blind angle of the user, and an effect tends to be achieved that the blind angle of the user can be compensated. It is preferred that the information processing apparatus 100-1 be caused to adhere to, for example, the vicinity of a temple of the user such that the camera is turned sideways.

Moreover, examples of the point to which the information processing apparatus 100-2 including the display function is caused to adhere include a point with which the user him/herself can observe the displayed image, such as, for example, the back of a hand. When the user desires to visually observe a displayed image during an operation by the user using the right hand or the dominant arm of the user, it is preferred that the information processing apparatus 100-2 be caused to adhere to the back of the left hand or the arm other than the dominant arm of the user.

Moreover, the information processing apparatus 100-1 may also include a microphone that picks up the surrounding sounds, together with the camera or the imaging function. In this case, the information processing apparatus 100-2 may output the video image imaged by the information processing apparatus 100-1 and the audio together with each other.

The information processing apparatus 100-1 and the information processing apparatus 100-2 execute direct communication with each other using the biological communication or the short-distance wireless communication, and thereby operate in cooperation with each other. Otherwise, the information processing apparatus 100-1 and the information processing apparatus 100-2 can also communicate with each other through another information terminal held by the user such as a smartphone to realize the operation in cooperation.

Figure 10:
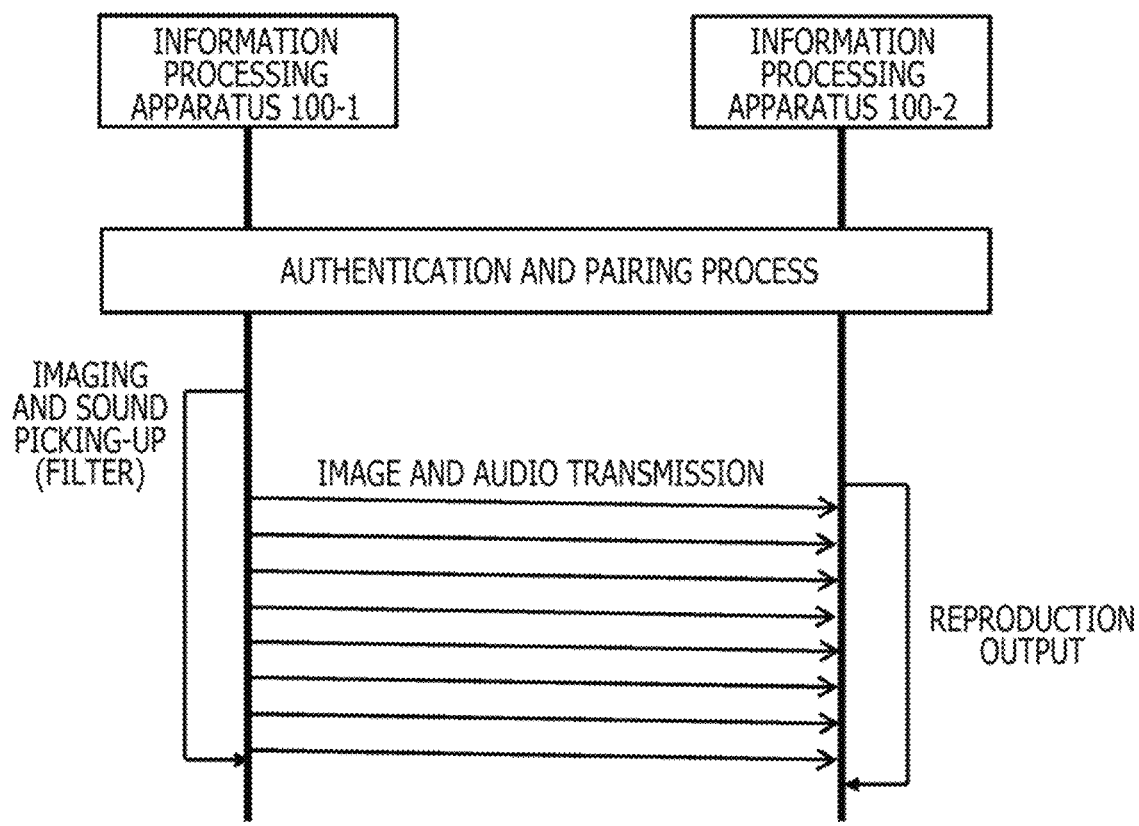
FIG. 10 is a diagram depicting an exemplary communication sequence executed when an information processing apparatus 100-1 and an information processing apparatus 100-2 cooperate with each other.

FIG. 10 depicts an exemplary communication sequence executed when the two of the information processing apparatus 100-1 and the information processing apparatus 100-2 cooperate with each other. It is also assumed that the cooperation is established through another information terminal while, in FIG. 10, for simplification of the drawing, the information processing apparatus 100-1 and the information processing apparatus 100-2 communicate directly with each other or the other information terminal is not depicted.

For example, when the state is established where the information processing apparatus 100-1 and the information processing apparatus 100-2 concurrently adheres to the body of the same user, the authentication process and the process for pairing are started up between the information processing apparatus 100-1 and the information processing apparatus 100-2 automatically or by any one of manual operations by the user (including an instruction using a sound), and the state is established where the information processing apparatus 100-1 and the information processing apparatus 100-2 cooperate with each other, through the above processes.

In the state of the cooperation, the image and the audio data may always be continuously transmitted from the information processing apparatus 100-1 to the information processing apparatus 100-2, and the information processing apparatus 100-2 may also always continuously reproduce and output the received image and audio data. It is however worried that the processing load on the apparatus is heavy to consume the battery when the image and the audio data are always continuously transmitted. Among all, the processing load of the image data is heavy. It is also worried that the communication band is continuously used. Filtering may therefore be executed for the image and the audio data using the biological information of the user.

The information processing apparatus 100-2 can also be enabled to execute the filtering for the received data while it is efficient for the overall system to execute the filtering before the transmission from the information processing apparatus 100-1. Moreover, the biological information of the user may also be detected using the biological sensor included in either the information processing apparatus 100-1 or the information processing apparatus 100-2. Otherwise, the filtering can also be executed using the biological information detected by another information processing apparatus concurrently adhering to the same user.

In addition, in the above, for simplification of the description, the Example has been taken where the two information processing apparatuses 100-1 and 100-2 cooperate with each other while an Example is also surely assumed where three or more information processing apparatuses cooperate with each other that concurrently adhere to the same user.

Example 6

The high-specification configuration method for the information processing apparatus 100 for as many types of sensor element and actuator element as possible to be included therein is considered assuming that the information processing apparatus 100 is applied to each of many adhesion points (described above). In the case where such a configuration method is employed, the sensor elements and the actuator elements that are essentially or preferably operated and, in contrast, the sensor elements and the actuator elements that do not need to be operated are present in accordance with the point for the actual adhesion.

When the sensor elements and the actuator elements to be preferably operated are not caused to operate, the user cannot enjoy the full benefit provided thereto by the adhesion of the information processing apparatus 100 to the body of the user. Moreover, when the sensor elements and the actuator elements that do not need to be operated are continuously operated, the battery is consumed.

The high-specification information processing apparatus 100 is adapted to automatically recognize or manually (including an instruction by the sound from the user) recognize the point for the adhesion on the body of the user and thereby controls the switching of the turning on or off of each of these sensor elements and the actuator elements. Moreover, the complete switching of the turning on or off of each of the sensor elements and the actuator elements is not controlled but control may be executed according to which the sensitivity of each of the sensors is switched stepwise and the output level of each of the actuator is switched stepwise in accordance with the purpose of use estimated from the point for the adhesion, or the like.

For example, a specific (or a predetermined number or more of biological sensors are started up as the start-up process for the information processing apparatus 100, and the control part estimates the adhesion point on the basis of the detected biological information (or a combination of plural pieces of detected biological information). The control part next turns on the necessary sensor elements and actuator elements, and turns off the unnecessary sensor elements and actuator elements on the basis of the estimated adhesion point.

Otherwise, the control part estimates the adhesion point for the main body of the information processing apparatus 100 on the basis of the vibration data detected by the vibration sensor, and turns on the necessary sensor elements and actuator elements and turns off the unnecessary sensor elements and actuator elements on the basis of the estimated adhesion point.

For each of the points to which the main body of the information processing apparatus 100 adheres, the characteristic of the vibration data differs and an action recognition algorism based on the vibration data also naturally differs. The control part therefore may execute the action recognition for the user on the basis of the vibration data by applying the recognition algorism in accordance with the adhesion point estimated by the control part and may further execute learning of the action recognition on the basis of the vibration data.

Moreover, the control part may execute driving control in accordance with the action recognition result using the actuator elements started up in accordance with the adhesion point, and may feed back the action recognition result to the user or may execute services such as provision of information based on the action recognition result.

Figure 11:
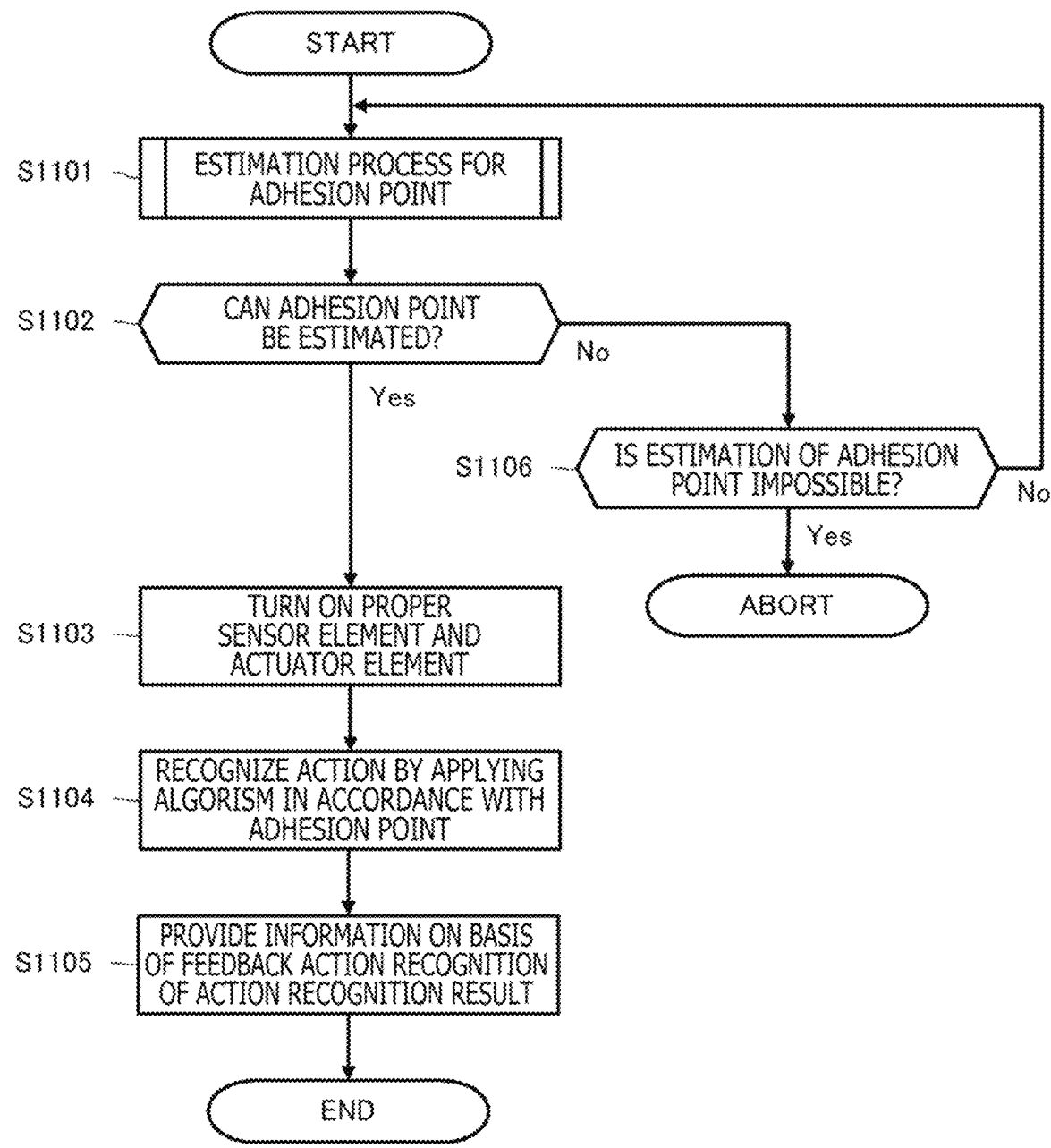
FIG. 11 is a flowchart depicting a process procedure in accordance with the adhesion point for the information processing apparatus 100.

FIG. 11 depicts, in the form of a flowchart, a process procedure in accordance with the adhesion point for the information processing apparatus 100. It is assumed that the depicted process procedure is executed led by, for example, the control part of the information processing apparatus 100.

The control part first executes a recognition process for the adhesion point for the main body of the information processing apparatus 100 using the automatic recognition or the manual recognition (step S1101).

At step S1101, the control part starts up a specific (or a predetermined number or more of biological sensors and the control part estimates the adhesion point for the main body of the information processing apparatus 100 on the basis of the detected biological information (or a combination of plural pieces of detected biological information). Otherwise, the control part estimates the adhesion point for the main body of the information processing apparatus 100 on the basis of the manual recognition (including an instruction by a sound from the user). Otherwise, the control part estimates the adhesion point for the main body of the information processing apparatus 100 on the basis of the vibration data detected by the vibration sensor.

Concerning the above, the control part checks whether or not the adhesion point for the main body of the information processing apparatus 100 can be estimated (step S1102). In the case where the adhesion point cannot be estimated (No of step S1102), the control part further checks whether or not the estimation of the adhesion point is impossible (step S1106).

When the estimation of the adhesion point is not impossible (No of step S1106), the procedure returns to step S1101 to continue the estimation process for the adhesion point. Moreover, in the case where the estimation of the adhesion point is impossible (Yes of step S1106), the control part causes this process to come to an end (ABORT). For example, in the case where the adhesion point cannot be estimated within a predetermined time period or a predetermined number of trials, it is determined that the estimation is impossible. Otherwise, in the case where the estimation of the adhesion point is impossible, a combination of the sensor elements and the actuator elements determined in advance may also be turned on not on the basis of the estimation result.

On the other hand, in the case where the adhesion point for the main body of the information processing apparatus 100 can be estimated (Yes of step S1102), the control part turns on the necessary sensor elements and actuator elements and turns off the unnecessary sensor elements and actuator elements on the basis of the estimated adhesion point (step S1103).

Thereafter, the control part applies the recognition algorism in accordance with the adhesion point estimated at step S1101 to execute the action recognition for the user on the basis of the vibration data (step S1104).

The control part thereafter executes the driving control in accordance with the action recognition result using the actuator elements started up in accordance with the adhesion point at step S1103, and feeds back the action recognition result to the user or executes the services such as the provision of the information based on the action recognition result (step S1105).

In addition, because the calculation load of each of the action recognition process and the learning process is large, these processes may be executed not by the information processing apparatus 100 configured to be relatively inexpensive and small but by another information terminal held by the user such as a smartphone.

Figure 12:
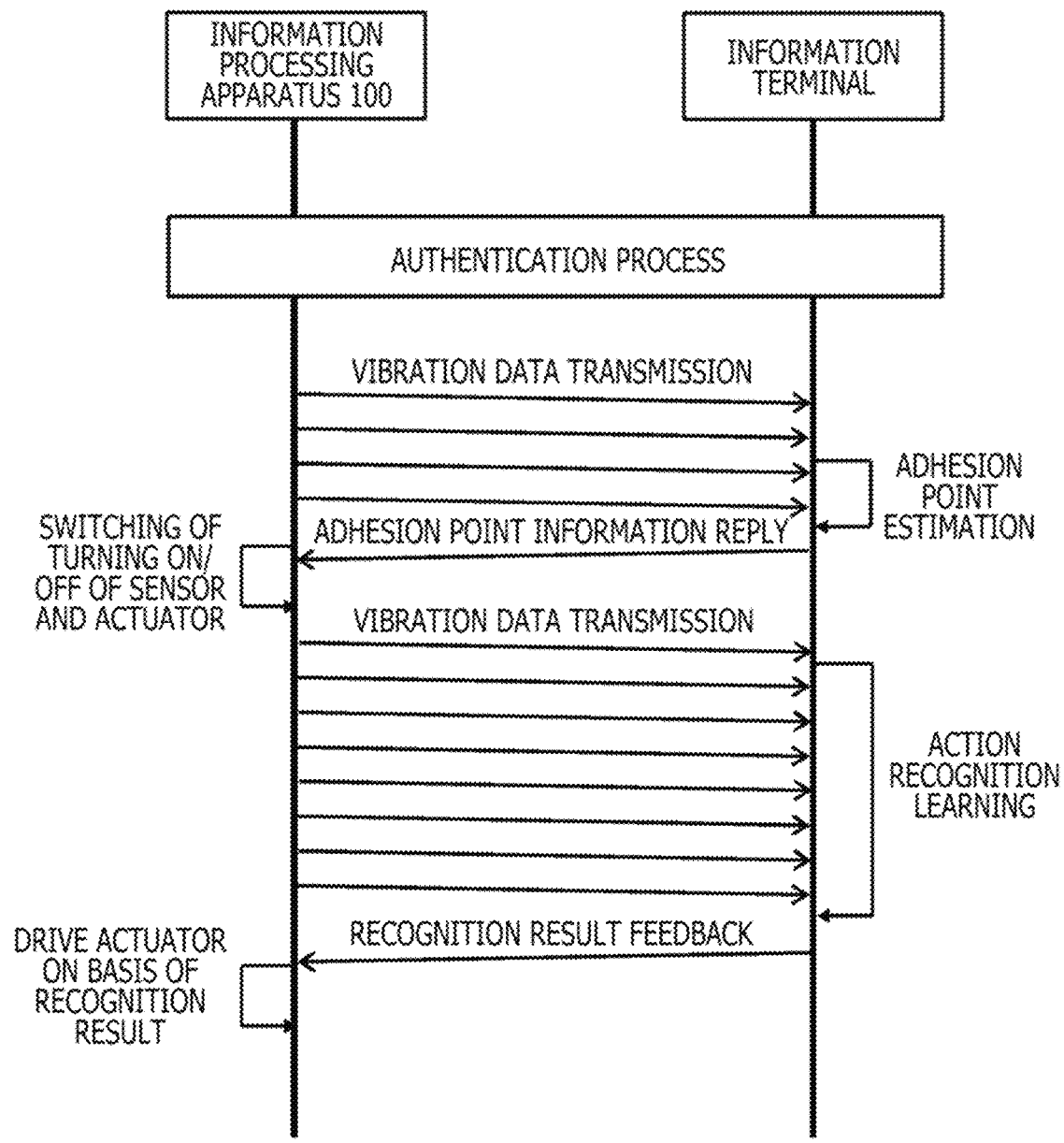
FIG. 12 is a diagram exemplifying a communication sequence executed when processing vibration data detected by a vibration sensor of the information processing apparatus 100 is executed on the other information terminal side.

FIG. 12 depicts an exemplary communication sequence executed when processing for vibration data detected by the vibration sensor of the information processing apparatus 100 is executed by the other information terminal. It is however assumed that the information processing apparatus 100 is mutually connected using Wi-Fi or another short-distance wireless communication.

Prior to the series of processes, the information processing apparatus 100 and the information terminal execute the authentication process.

When the authentication process is successfully executed, the information processing apparatus 100 continuously transmits the vibration data detected by the vibration sensor of the information processing apparatus 100, to the information terminal for a predetermined time period.

When the information terminal extracts the characteristic data from the vibration data received from the information processing apparatus 100 and estimates the point to which the information processing apparatus 100 adheres on the basis of the temporal sequence information of the characteristic data, the information terminal replies the information processing apparatus 100 about the estimation result.

The information processing apparatus 100 turns on the necessary sensor elements and actuator elements and turns off the unnecessary sensor elements and actuator elements in accordance with the adhesion point estimated by the information terminal.

The information processing apparatus 100 thereafter also continuously transmits the vibration data detected by the vibration sensor of the information processing apparatus 100 to the information terminal.

The information terminal executes the action recognition for the user on the basis of the vibration data in accordance with the adhesion point for the information processing apparatus 100 estimated previously by the information terminal, and further executes the learning for the action recognition on the basis of the vibration data. The information terminal thereafter stores in the terminal the result of the action recognition and the learning result as information relating to the action history of the user. Moreover, the information terminal feeds back the result of the action recognition and the learning result to the information processing apparatus 100.

The information processing apparatus 100 executes the driving control for the actuator elements in accordance with the action recognition result fed back from the information terminal, and feeds back the action recognition result to the user or executes the services such as the information provision on the basis of the action recognition result.

Example 7

The information processing apparatus 100 is used as a stand-alone life log recording apparatus being caused to adhere to the surface of the body of the user and, on the other hand, can also be used by being connected to another information terminal such as a smartphone held by the user, a cloud (such as a server installed on the Internet), and the like. The information processing apparatus 100 is connected to the other information terminal or the cloud and thereby enables realization of the processes that are difficult for a stand-alone apparatus, using these calculation resources, and various types of services are enabled to be provided to the user.

A connection procedure for the information processing apparatus 100 and an external apparatus therebetween will be described below as a seventh Example.

Figure 13:
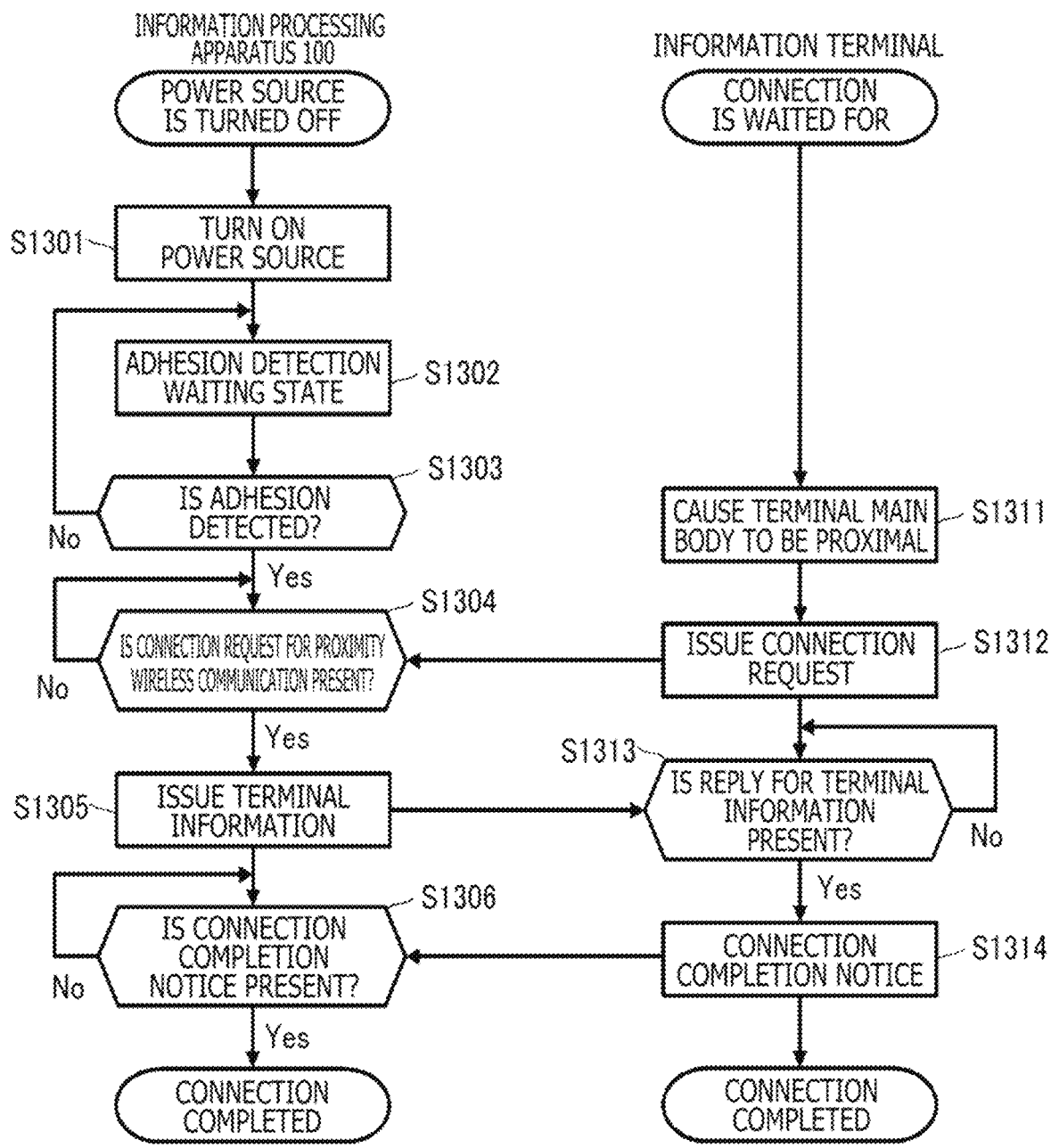
FIG. 13 is a diagram exemplifying a connection procedure for the information processing apparatus and an information terminal held by a user.

FIG. 13 exemplifies a process procedure for connecting the information processing apparatus 100 and an information terminal held by the user (such as a smartphone) with each other. In FIG. 13, the information processing apparatus 100 and the information terminal are however connected to each other using a proximity wireless communication technique such as NFC.

When the power source is turned on in response to the fact that the release paper sheet (described above) is peeled off from the paste face of the adhering part 103 (S1301), the information processing apparatus 100 enters an standby state for the adhesion detection that detects that the information processing apparatus 100 adheres to the surface of the body of the user using the adhering part 103 (S1302).

When the information processing apparatus 100 thereafter detects that the adhering part 103 adheres to the surface of the body of the user (Yes of step S1303), the information processing apparatus 100 next stands by for a connection request by the proximity wireless communication from the information terminal held by the same user such as a smartphone (step S1304).

The user causes the main body of the information terminal to be proximal to the main body of the information processing apparatus 100 by putting the main body in front of the main body of the information processing apparatus 100 adhering to the skin of the user (S1311). The information terminal thereafter issues a connection request to the information processing apparatus 100 using the proximity wireless communication (S1312).

When the information processing apparatus 100 receives the connection request from the information terminal (Yes of S1304), the information processing apparatus 100 issues terminal information including the information relating to the information processing apparatus 100 itself to the information terminal (S1305). The configuration of the terminal information is optional. The terminal information may include, for example, apparatus identification information identifying the information processing apparatus 100, user-specific information identifying the user having the main body of the information processing apparatus 100 adhering thereto, and the like.

When the information terminal can receive the terminal information from the information processing apparatus 100 that is the connection request destination (Yes of S1313), the information terminal transmits a connection completion notice to the information processing apparatus 100 (step S1314) and thereby completes the connection with the information processing apparatus 100. In addition, the information terminal may transmit the connection completion notice after executing verification or the authentication process for the terminal information received from the information processing apparatus 100.

Moreover, the information processing apparatus 100 receives the connection completion notice from the information terminal that is the connection request source (Yes of S1306) and thereby completes the connection with the information terminal.

Figure 14:
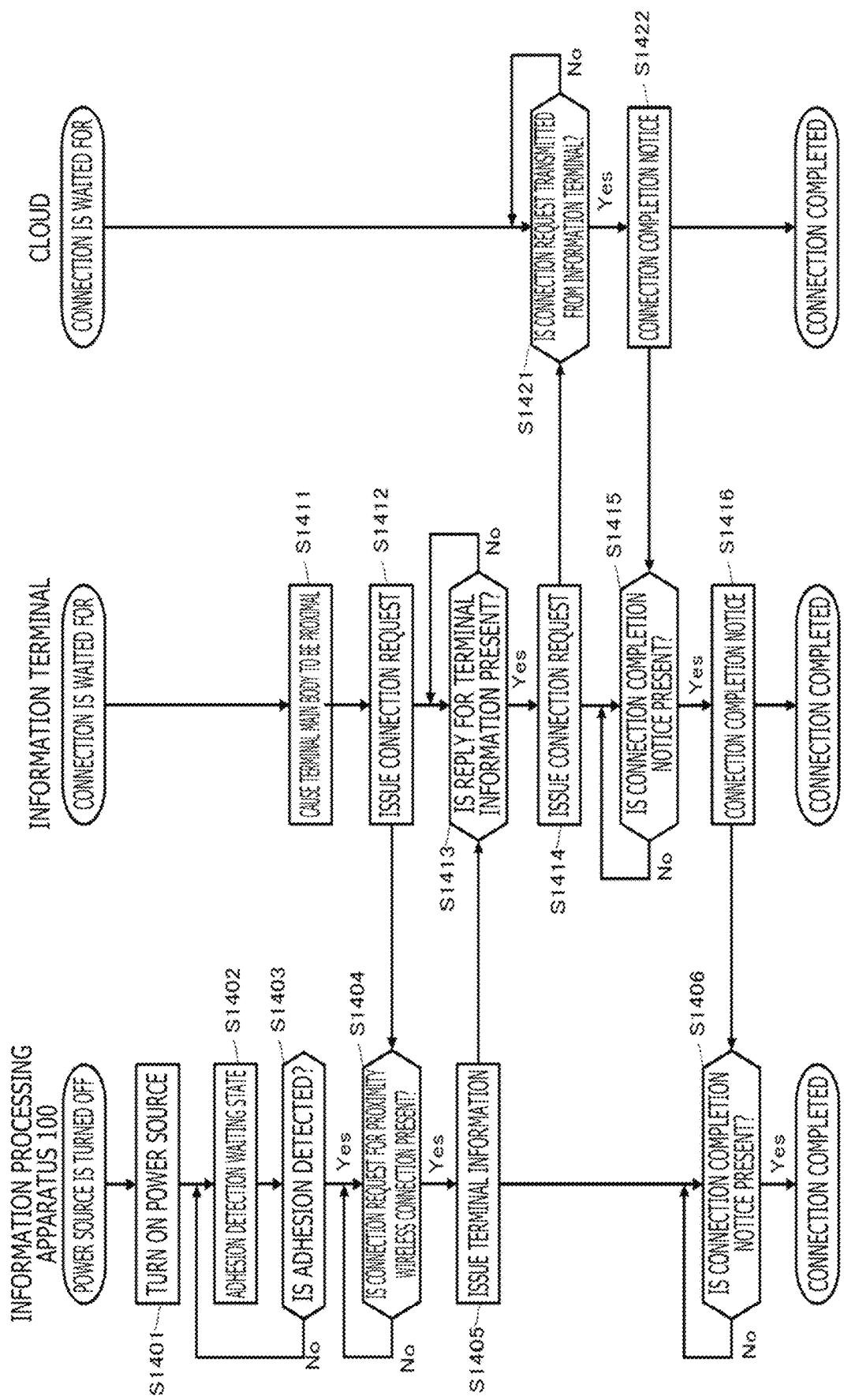
FIG. 14 is a diagram exemplifying a process procedure for connecting the information processing apparatus 100 and a cloud through the information terminal held by a user.

FIG. 14 exemplifies a process procedure for the information processing apparatus 100 and a cloud to be connected to each other through the information terminal held by the user (such as a smartphone). In FIG. 14, it is however assumed that the information processing apparatus 100 and the information terminal are connected to each other using a proximity wireless communication technique such as NFC, and the information terminal and the cloud are connected to each other through a wide area network such as the Internet.

When the power source is turned on in response to the fact that the release paper sheet (described above) is peeled off from the paste face of the adhering part 103 (S1401), the information processing apparatus 100 enters the standby state for the adhesion detection that detects that the information processing apparatus 100 adheres to the surface of the body of the user using the adhering part 103 (S1402).

When the information processing apparatus 100 thereafter detects that the adhering part 103 adheres to the surface of the body of the user (Yes of step S1403), the information processing apparatus 100 next stands by for a connection request by the proximity wireless communication from the information terminal held by the same user (step S1404).

The user causes the main body of the information terminal to be proximal to the main body of the information processing apparatus 100 by putting the main body in front of the main body of the information processing apparatus 100 adhering to the skin of the user (S1411). The information terminal thereafter issues the connection request to the information processing apparatus 100 using the proximity wireless communication (S1412).

When the information processing apparatus 100 receives the connection request from the information terminal (Yes of S1404), the information processing apparatus 100 issues terminal information including the information relating to the information processing apparatus 100 itself, to the information terminal (S1405).

When the information terminal can receive the terminal information from the information processing apparatus 100 that is the connection request destination (Yes of S1413), the information terminal next issues a connection request to the cloud (S1414).

When the cloud receives the connection request from the information terminal (Yes of S1421), the cloud transmits the connection completion notice to the information terminal (S1422) and thereby completes the connection with the information terminal (or the information processing apparatus 100 through the information terminal). In addition, the cloud may also transmit the connection completion notice after executing the verification or the authentication process for the information terminal and the information processing apparatus 100.

When the information terminal receives the connection completion notice from the cloud that is the connection request destination (Yes of S1415), the information terminal transmits a connection completion notice to the information processing apparatus 100 (S1416) and thereby completes the connection with the information processing apparatus 100.

Moreover, the information processing apparatus 100 receives the connection completion notice from the information terminal that is the connection request source (Yes of S1406) and thereby completes the connection with the information terminal.

Figure 15:
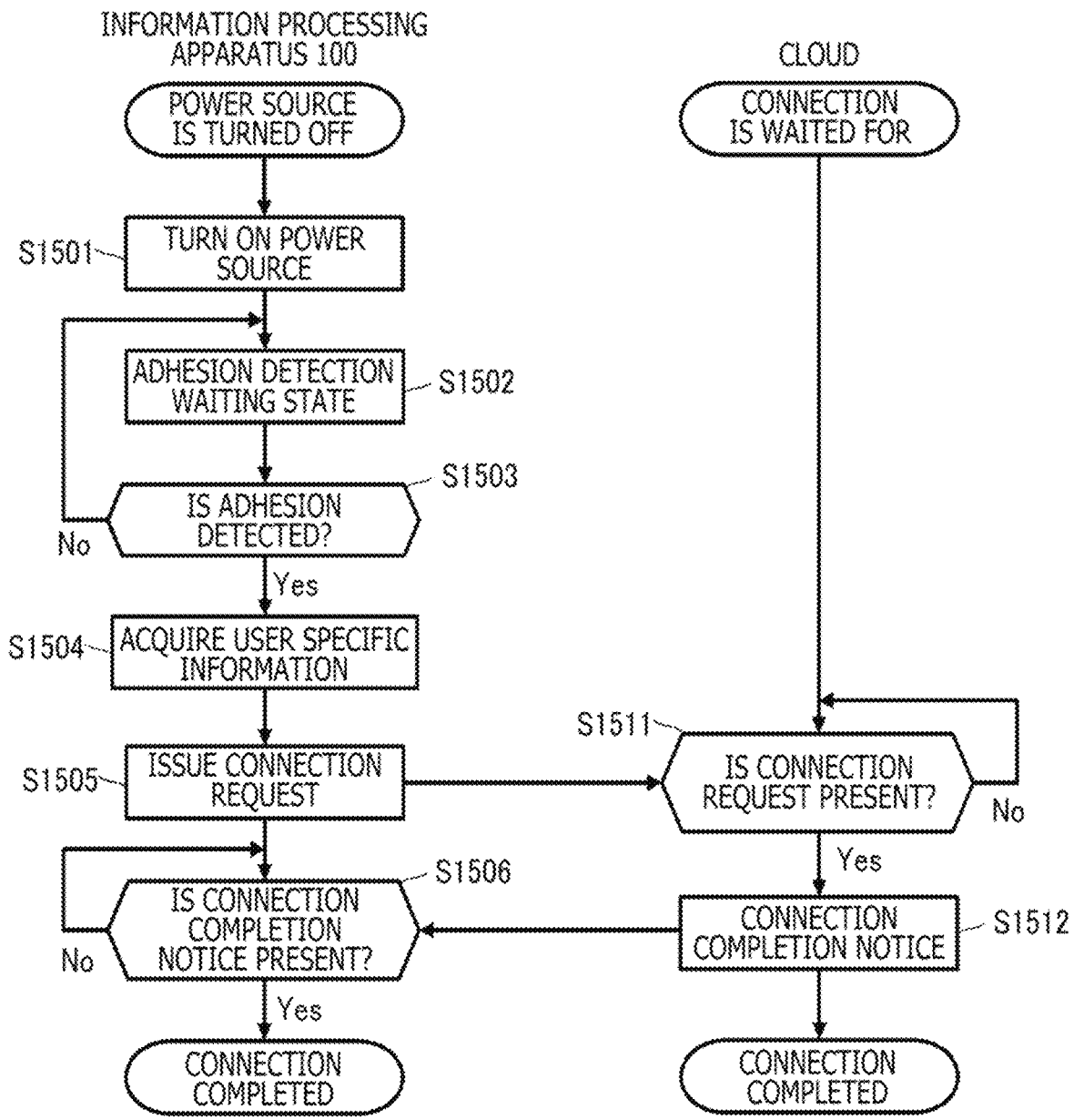
FIG. 15 is a diagram exemplifying a process procedure for connecting the information processing apparatus 100 and the cloud.

FIG. 15 exemplifies a process procedure for the information processing apparatus 100 and the cloud to be connected to each other. It is however assumed in FIG. 15 that the information processing apparatus 100 has the biological sensor for user authentication mounted thereon. In addition, similar to the connection procedure depicted in FIG. 14, the information processing apparatus 100 and the cloud may execute the connection through a relaying apparatus such as the information terminal held by the user while, in FIG. 15, for simplification of the description, the relaying apparatus is not depicted.

When the power source is turned on in response to the fact that the release paper sheet (described above) is peeled off from the paste face of the adhering part 103 (S1501), the information processing apparatus 100 enters an standby state for the adhesion detection that detects that the information processing apparatus 100 adheres to the surface of the body of the user using the adhering part 103 (S1502).

When the information processing apparatus 100 detects that the adhering part 103 adheres to the surface of the body of the user (Yes of step S1503), the information processing apparatus 100 next, using the biological sensor, acquires the biological information to be the information for user authentication, that is, the user-specific information from the body of the user using the biological sensor (step S1504). The information processing apparatus 100 thereafter issues a connection request including the user-specific information to the cloud (S1505).

When the cloud receives the connection request from the information processing apparatus 100 (Yes of S1511), the cloud transmits a connection completion notice to the information processing apparatus 100 (S1512) and thereby completes the connection with the information processing apparatus 100. At this time, the cloud may transmit the connection completion notice after executing the verification or the authentication process for the user-specific information of the user having the information processing apparatus 100 adhering thereto.

Moreover, the information processing apparatus 100 receives the connection completion notice of the cloud that is the connection request destination (Yes of S1506) and thereby completes the connection with the information terminal.

FIG. 16 exemplifies a process procedure for connecting the information processing apparatus 100 and the cloud to each other. The connection procedure depicted in FIG. 16 differs from the connection procedure depicted in FIG. 15 in the point that the accounts of the information processing apparatus 100 and the user having this adhering thereto are correlated with each other when the use of the information processing apparatus 100 is started (or at the time of its purchase). In addition, similar to the connection procedure depicted in FIG. 14, the information processing apparatus 100 and the cloud may execute the connection through a relaying apparatus such as the information terminal held by the user while, in FIG. 16, for simplification of the description, the relaying apparatus is not depicted.

When the power source is turned on in response to the fact that the release paper sheet (described above) is peeled off from the paste face of the adhering part 103 (S1601), the information processing apparatus 100 enters the standby state for the adhesion detection that detects that the information processing apparatus 100 adheres to the surface of the body of the user using the adhering part 103 (S1602).

When the information processing apparatus 100 detects that the adhering part 103 adheres to the surface of the body of the user (Yes of step S1603), the information processing apparatus 100 next acquires apparatus identification information uniquely identifying the information processing apparatus 100 from a memory in the control part (step S1604). The information processing apparatus 100 thereafter issues a connection request including the apparatus identification information and information relating to the user account to the cloud (S1605).

When the cloud receives the connection request from the information processing apparatus 100 (Yes of S1611), the cloud checks the received apparatus identification information and the user account and executes a correlation process for these (S1612). The cloud next transmits a connection completion notice to the information processing apparatus 100 that is the connection request source (S1613) and thereby completes the connection with the information processing apparatus 100.

Moreover, the information processing apparatus 100 receives the connection completion notice of the cloud that is the connection request destination (Yes of S1606) and thereby completes the connection with the information terminal.

INDUSTRIAL APPLICABILITY

The technique disclosed herein has been described in detail as above with reference to the specific embodiment. It is however obvious that those skilled in the art can achieve modifications and substitutions within the scope not departing from the gist of the technique disclosed herein.

The information processing apparatus disclosed herein is a wearable device used by being adhered to the surface (the skin) of the body and is used by being adhered to each of the regions such as, for example, a temple, the glabella, the back of an ear, a region beneath the jaw, the neck, the root of the neck, the throat portion, an upper arm, a forearm, a wrist, the back of a hand, and the abdomen. Moreover, a similar information processing apparatus can be utilized as an IoT device by causing this information processing apparatus to adhere to not the human body but each of various machines and articles.

In short, the technique disclosed herein has been described using the form of exemplification and the content of the description herein should not be interpreted to be limiting. To determine the gist of the technique disclosed herein, the appended claims should be taken into consideration.

In addition, the technique disclosed herein can also take the following configurations.

(1) An information processing apparatus including:
a sound pickup sensor that has a sound pickup function;
a communicating part that wirelessly transmits audio data picked up by the sound pickup sensor to the outside;
a control part that controls the sound pickup sensor and the communicating part;
a power source part that supplies a power source to at least one of the sound pickup sensor, the communicating part, or the control part;
a housing part that accommodates therein at least one of the sound pickup sensor, the communicating part, the control part, or the power source part; and
an adhering part that fixes the housing part to a user.

(2) The information processing apparatus according to the above (1), in which
the sound pickup sensor is able to pick up a sound using flesh conduction of the user.

(3) The information processing apparatus according to any of the above (1) or (2), further including:
an biological sensor that detects biological information of the user, in which
the control part controls processing for the audio data picked up by the sound pickup sensor on the basis of the biological information detected by the biological sensor.

(4) The information processing apparatus according to the above (3), in which the control part controls intermittent reproduction of the audio data on the basis of biological information detected by the biological sensor.

(5) The information processing apparatus according to any of the above (3) or (4), in which the control part controls such that an integrated signal having the audio data and the biological information synchronized with each other in the temporal direction is produced and is output through the communicating part.

(6) The information processing apparatus according to any of the above (1) to (5), further including:
an adhesion sensor that detects an adhesion state with the user in the adhering part, in which
the control part controls an operation of the information processing apparatus in accordance with the adhesion state detected by the adhesion sensor.

(7) The information processing apparatus according to any of the above (1) to (6), further including:
an actuator.

(8) The information processing apparatus according to the above (7), including:
a speaker as the actuator, wherein
the housing part is fixed to the back of an ear of the user by the adhering part.

(9) The information processing apparatus according to any of the above (7) or (8), including:
a displaying part as the actuator.

(10) The information processing apparatus according to any of the above (1) to (9), further including:
an imaging sensor.

(11) The information processing apparatus according to any of the above (1) to (10), further including:
plural types of sensors and plural types of actuators, in which
the control part controls the plural types of sensors and the plural types of actuators.

(12) The information processing apparatus according to the above (11), in which
the control part controls at least turning on or off of each of the sensors and the actuators in accordance with a point at which the housing part is fixed to the user using the adhering part.

(13) The information processing apparatus according to the above (11), further including:
a vibration sensor, in which
the control part controls at least turning on or off of each of the sensors and the actuators in accordance with a fixation point recognized on the basis of vibration data of the body of the user detected by the vibration sensor.

(14) The information processing apparatus according to any of the above (1) to (13), in which
the housing part has flexibility.

(14-1) The information processing apparatus according to any of the above (1) to (14), in which
the housing part has a water-shedding property.

(14-2) The information processing apparatus according to any of the above (1) to (14), in which
the surface of the housing part is in a skin color.

(15) The information processing apparatus according to any of the above (1) to (14), further including:

a substrate part that has circuit pieces mounted thereon including the sound pickup sensor, the communicating part, and the control part, in which the housing part accommodates therein the substrate part.

(16) The information processing apparatus according to the above (15), in which the substrate part includes slits in at least two directions and has flexibility or stretchability.

(17) The information processing apparatus according to any of the above (1) to (16), in which the adhering part includes one or more apertures.

(18) The information processing apparatus according to any of the above (1) to (17), further including:

a body fluid processing part that is stacked on the adhering part.

(18-1) The information processing apparatus according to the above (18), in which the body fluid processing part has a moisture absorbing property or moisture permeability.

(18-2) The information processing apparatus according to the above (18), in which the body fluid processing part includes a mesh material that guides a body fluid using the capillary activity.

(18-3) The information processing apparatus according to the above (18), in which the body fluid processing part includes a high-molecule polymer moisture absorbing material.

(19) A control method for an information processing apparatus including a sound pickup sensor that has a sound pickup function; a communicating part that wirelessly transmits audio data picked up by the sound pickup sensor to the outside; a power source part that supplies a power source to at least one of the sound pickup sensor, the communicating part, or the control part; a housing part that accommodates therein at least one of the sound pickup sensor, the communicating part, the control part, or the power source part; and an adhering part that fixes the housing part to a user, the control method including steps of:

processing the audio data picked up by the sound pickup sensor, and controlling transmission and reception processes through the communicating part.

(20) A recording medium that records thereon a computer program to control an information processing apparatus including a sound pickup sensor that has a sound pickup function; a communicating part that wirelessly transmits audio data picked up by the sound pickup sensor to the outside; a power source part that supplies a power source to at least one of the sound pickup sensor, the communicating part, or the control part; a housing part that accommodates therein at least one of the sound pickup sensor, the communicating part, the control part, or the power source part; and an adhering part that fixes the housing part to a user, in which the computer program is described in a computer readable format to cause a computer to execute steps of:

processing the audio data picked up by the sound pickup sensor, and controlling transmission and reception processes through the communicating part.

REFERENCE SIGNS LIST

100 . . . Information processing apparatus
101 . . . Electric part,
102 . . . Housing part
103 . . . Adhering part,
104 . . . Body fluid processing part
310 . . . Sensor part
311 . . . First sensor part,
312 . . . Second sensor part
320 . . . Actuator part
321 . . . First actuator part,
322 . . . Second actuator part
330 . . . Communicating part
400 . . . Substrate,
401 . . . Sound pickup sensor,
402 . . . Control part
403 . . . Chip antenna,
404 . . . Power source part

The invention claimed is:

1. An information processing apparatus, comprising:
a plurality of types of sensors, wherein
a first type of sensor of the plurality of types of sensors is a sound pickup sensor, and
the sound pickup sensor is configured to pick up audio data;
a plurality of types of actuators;
a communicating part configured to wirelessly transmit the audio data picked up by the sound pickup sensor to an outside of the information processing apparatus;
a control part configured to:
control the plurality of types of sensors, the plurality of types of actuators, and the communicating part; and
control at least one of turn on or turn off of each of the plurality of types of sensors and each of the plurality of types of actuators;
a power source part a configured to supply power to at least one of the sound pickup sensor, the communicating part, or the control part;
a housing part that accommodates therein at least one of the sound pickup sensor, the communicating part, the control part, or the power source part; and
an adhering part configured to fix the housing part to a user at an adhesion point, wherein
the control of the at least one of the turn on or the turn off is based on the adhesion point at which the housing part is fixed to the user.

2. The information processing apparatus according to claim 1,
wherein the sound pickup sensor is further configured to pick up a sound based on flesh conduction of the user.

3. The information processing apparatus according to claim 1, wherein
a second type of sensor of the plurality of types of sensors is a biological sensor,
the biological sensor is configured to detect biological information of the user, and
the control part is further configured to control process of the audio data based on the biological information detected by the biological sensor.

4. The information processing apparatus according to claim 3,
wherein the control part is further configured to control intermittent reproduction of the audio data based on the biological information detected by the biological sensor.

5. The information processing apparatus according to claim 3, wherein
the control part is further configured to:
control generation of an integrated signal; and
control output of the integrated signal via the communicating part, the integrated signal includes the audio data and the biological information, and the audio data is synchronized with the biological information in a temporal direction.

6. The information processing apparatus according to claim 1, wherein a second type of sensor of the plurality of types of sensors is an adhesion sensor, the adhesion sensor is configured to detect an adhesion state of the adhering part with the user, and the control part is further configured to control an operation of the information processing apparatus based on the adhesion state detected by the adhesion sensor.

7. The information processing apparatus according to claim 1, wherein a type of actuator of the plurality of types of actuators is a speaker, and the housing part is fixed to a back of an ear of the user by the adhering part.

8. The information processing apparatus according to claim 1, wherein a type of actuator of the plurality of types of actuators is a displaying part.

9. The information processing apparatus according to claim 1, wherein a second type of sensor of the plurality of types of sensors is an imaging sensor.

10. The information processing apparatus according to claim 1, wherein a second type of sensor of the plurality of types of sensors is a vibration sensor, the vibration sensor is configured to detect vibration data of a body of the user, and the control part is further configured to recognize the adhesion point based on the vibration data of the body of the user.

11. The information processing apparatus according to claim 1, wherein the housing part has flexibility.

12. The information processing apparatus according to claim 1, further comprising a substrate part that includes circuit pieces, wherein the circuit pieces are on the substrate part, the circuit pieces include the sound pickup sensor, the communicating part, and the control part, and the housing part accommodates therein the substrate part.

13. The information processing apparatus according to claim 12, wherein the substrate part further includes slits in at least two directions, and the substrate part has at least one of flexibility or stretchability.

14. The information processing apparatus according to claim 1, wherein the adhering part includes at least one aperture.

15. The information processing apparatus according to claim 1, further comprising a body fluid processing part on the adhering part.

16. A control method, comprising:

in an information processing apparatus:

picking up, by a sound pickup sensor of the information processing apparatus, audio data, wherein the sound pickup sensor is a type of sensor of a plurality of types of sensors of the information processing apparatus;

controlling, by a control part of the information processing apparatus, process of the audio data;

wirelessly transmitting, by a communicating part of the information processing apparatus, the audio data picked up by the sound pickup sensor to an outside of the information processing apparatus;

controlling, by the control part, the plurality of types of sensors, a plurality of types of actuators of the information processing apparatus, and the communicating part;

controlling, by the control part, at least one of turn on or turn off of each of the plurality of types of sensors and each of the plurality of types of actuators;

controlling, by the control part, a reception process via the communicating part;

supplying, by a power source part of the information processing apparatus, power to at least one of the sound pickup sensor, the communicating part, or the control part, wherein a housing part of the information processing apparatus accommodates therein at least one of the sound pickup sensor, the communicating part, the control part, or the power source part; and fixing, by an adhering part of the information processing apparatus, the housing part to a user at an adhesion point, wherein the control of the at least one of the turn on or the turn off is based on the adhesion point at which the housing part is fixed to the user.

17. A non-transitory computer-readable medium having stored thereon computer-executable instructions which, when executed by an information processing apparatus, cause the information processing apparatus to execute operations, the operations comprising:

picking up, by a sound pickup sensor of the information processing apparatus, audio data, wherein the sound pickup sensor is a type of sensor of a plurality of types of sensors of the information processing apparatus;

controlling, by a control part of the information processing apparatus, process of the audio data;

wirelessly transmitting, by a communicating part of the information processing apparatus, the audio data picked up by the sound pickup sensor to an outside of the information processing apparatus;

controlling, by the control part, the plurality of types of sensors, a plurality of types of actuators of the information processing apparatus, and the communicating part;

controlling, by the control part, a reception process via the communicating part;

controlling, by the control part, at least one of turn on or turn off of each of the plurality of types of sensors and each of the plurality of types of actuators; and supplying, by a power source part of the information processing apparatus, power to at least one of the sound pickup sensor, the communicating part, or the control part, wherein a housing part of the information processing apparatus accommodates therein at least one of the sound pickup sensor, the communicating part, the control part, or the power source part, an adhering part of the information processing apparatus is configured to fix the housing part to a user at an adhesion point, and the control of the at least one of the turn on or the turn off is based on the adhesion point at which the housing part is fixed to the user.

18. An information processing apparatus, comprising:
a sound pickup sensor configured to pick up audio data;
a biological sensor configured to detect biological information of a user;
a communicating part configured to wirelessly transmit the audio data picked up by the sound pickup sensor to an outside of the information processing apparatus;
a control part configured to:
  control the sound pickup sensor and the communicating part;
  control process of the audio data based on the biological information detected by the biological sensor;
  control generation of an integrated signal; and
  control output of the integrated signal via the communicating part, wherein
    the integrated signal includes the audio data and the biological information, and
    the audio data is synchronized with the biological information in a temporal direction;
a power source part configured to supply power to at least one of the sound pickup sensor, the communicating part, or the control part;
a housing part that accommodates therein at least one of the sound pickup sensor, the communicating part, the control part, or the power source part; and
an adhering part configured to fix the housing part to the user.

* * * * *